United States Patent
Pan et al.

(10) Patent No.: US 11,634,468 B2
(45) Date of Patent: Apr. 25, 2023

(54) PARATHYROID HORMONE VARIANTS

(71) Applicant: Shire-NPS Pharmaceuticals, Inc., Lexington, MA (US)

(72) Inventors: Clark Pan, Sudbury, MA (US); Angela Norton, Reading, MA (US); Kevin Holmes, Belmont, MA (US); David Bruce Lloyd, Leland, NC (US); Bryan James Goodwin, Lexington, MA (US); Rongxin Shi, Waltham, MA (US); Sujit Jain, Lexington, MA (US); Chuan Shen, West Roxbury, MA (US)

(73) Assignee: SHIRE-NPS PHARMACEUTICALS, INC., Lexington, MA (US)

( * ) Notice: Subject to any disclaimer, the term of this patent is extended or adjusted under 35 U.S.C. 154(b) by 122 days.

(21) Appl. No.: 16/776,107

(22) Filed: Jan. 29, 2020

(65) Prior Publication Data
US 2020/0247865 A1  Aug. 6, 2020

Related U.S. Application Data

(60) Provisional application No. 62/798,113, filed on Jan. 29, 2019, provisional application No. 62/800,744, filed on Feb. 4, 2019, provisional application No. 62/884,730, filed on Aug. 9, 2019.

(51) Int. Cl.
| | |
|---|---|
| *C07K 14/635* | (2006.01) |
| *A61K 9/00* | (2006.01) |
| *A61P 5/18* | (2006.01) |
| *C07K 1/16* | (2006.01) |
| *A61K 38/00* | (2006.01) |

(52) U.S. Cl.
CPC .......... *C07K 14/635* (2013.01); *A61K 9/0014* (2013.01); *A61P 5/18* (2018.01); *C07K 1/165* (2013.01); *A61K 38/00* (2013.01); *C07K 2319/30* (2013.01)

(58) Field of Classification Search
None
See application file for complete search history.

(56) References Cited

U.S. PATENT DOCUMENTS 9,579,392 B2 * 2/2017 Culbertson ............. A61P 43/00

FOREIGN PATENT DOCUMENTS

| WO | 2017148883 | 6/2017 |
| WO | 2017218977 | 12/2017 |

OTHER PUBLICATIONS

International Search Report dated Jun. 23, 2020 in connection with PCT International Application No. PCT/US20/15634.
Written Opinion dated Jun. 23, 2020 in connection with PCT International Application No. PCT/US20/15634.

* cited by examiner

*Primary Examiner* — Maury A Audet
(74) *Attorney, Agent, or Firm* — Troutman Pepper Hamilton Sanders LLP

(57) ABSTRACT

The invention relates to parathyroid hormone (PTH) variants and pharmaceutical compositions comprising same. The invention further relates to PTH compositions with improved serum half-life and peak-trough ratios, and methods of controlling serum calcium levels with the PTH variants and compositions of the invention. The invention further relates to methods of treating hypoparathyroidism and/or hypocalcemia due to hypoparathyroidism with the PTH variants and compositions of the invention.

5 Claims, 21 Drawing Sheets
(17 of 21 Drawing Sheet(s) Filed in Color)
Specification includes a Sequence Listing.

FIGURE 13A
High-throughput screening (HTS) of Capto Adhere ImpRes and Capto MMC ImpRes using Predictor Plates
AKTA benchtop runs guided by HTS
Pilot scale production
FIGURE 13B
ATF Harvest
In-line Concentration
Protein A Capture
VI and Neutralization
Polishing 1
Polishing 2
Virus Filtration
Final UFDF/DS

- Binding is better away from pI and with low salt
- The optimal binding condition is 50 mM MES, pH 6.0 without any salt

- Binding seen across pH range, salt impact moderate
- The optimal flow-through condition is 50 mM acetate, pH 5.0 without any salt

PARATHYROID HORMONE VARIANTS

CROSS-REFERENCE TO RELATED APPLICATIONS

This application claims benefit to U.S. Provisional Application Nos. 62/798,113, filed Jan. 29, 2019, 62/800,744, filed Feb. 4, 2019, and 62/884,730, filed Aug. 9, 2019, the contents of each of which are hereby incorporated by reference.

FIELD OF INVENTION

The present invention relates to parathyroid hormone variants and compositions comprising same. The invention further relates to parathyroid hormone variants and compositions with improved serum half-life and methods of controlling serum calcium levels with the parathyroid hormone compositions of the invention.

SEQUENCE LISTING

This application contains a Sequence Listing which has been submitted in ASCII format via EFS-Web and is hereby incorporated by reference herein in its entirety. The ASCII text file was created on Mar. 11, 2020, is named 250501_000164_SL.TXT and is 26 kilobytes in size.

BACKGROUND OF THE INVENTION

Parathyroid hormone (PTH) is a secreted, 84 amino acid product of the mammalian parathyroid gland that controls serum calcium levels through its action on various tissues, including bone. Studies in humans with certain forms of PTH have demonstrated an anabolic effect on bone and have prompted significant interest in its use for the treatment of osteoporosis and related bone disorders, as well as hypoparathyroidism.

It is known that the first 34 N-terminal amino acids have the same activation as the full length PTH(1-84) at the only known receptor for PTH, "PTH1R". See, for instance, Potts et al., Amer. Journ. of Med., 50: 639-649 (1971); Potts et al., Proceed. of the 3rd Intern. Symp. of Endocrin., London, pp 333-349 (1971); Tregear et al., Endocrin., 93: 1349-1353 (1973). In addition, it has been shown that C-terminal fragments, such as 39-84 and 53-84, do not compete with the 1-34 fragment for receptor binding. Furthermore, these C-terminal fragments did not activate adenylate cyclase, all of which led to the conclusion that the C-terminal portion of the PTH peptide was irrelevant. See, Segre et al., Journ. of Bio. Chem., 254: 6980-6986 (1979); Nissenson et al., Journ. of Bio. Chem., 254: 1469-1475 (1979); Potts et al., Adv. in Prot. Chem., 35: 323-396 (1982).

However, even though the C-terminal end of PTH was deemed to not be relevant to biological activity, it has been found that the C-terminal portion of the peptide is necessary for normal transport and processing. See, for instance, Kemper et al., Proceed. of the Nat. Acad. of Sciences, 71: 3731-3735 (1974); Freeman et al., Molec. Endocrin., 1: 628-638 (1987); Wiren et al., Journ. of Bio. Chem., 263: 19771-19777 (1988); Cioffi et al., Journ. of Bio. Chem., 264: 15052-15058 (1989); Karaplis et al., Journ. of Bio. Chem., 270: 1629-1635 (1995); Lim et al., Endocrin., 131: 2325-2330 (1992). In particular, there is evidence that full-length PTH is cleaved to C-terminal fragments within the parathyroid gland, and that these fragments are secreted in response to increased calcium ion concentrations in the blood. There is no evidence to date that N-terminal fragments are stored within or secreted from the gland except in the form of intact PTH. See Habener et al., Nature—New Biol., 238: 152-154 (1972); Flueck et al., Journ. of Clin. Invest., 60: 1367-1375 (1977); Mayer et al., Endocrin., 104: 1778-1784 (1979); Chu et al., Endocrin., 93: 915-924 (1973); Habener et al., Endocrin., 97: 431-441 (1975); Russell et al., Journ. of Clin. Invest., 72: 1851-1855 (1983); Heinrich et al., Endocrin., 112: 449-458 (1983); Brookman et al., Journ. of Bone & Min. Res., 1: 529-537 (1986); Sherwood et al., Proceed. of the Nat. Acad. of Sciences, 67: 1631-1638 (1970); Arnaud et al., Amer. Journ. of Med., 50: 630-638 (1971); Hanley et al., Journ. of Clin. Invest., 62: 1247-1254 (1978); Di Bella et al., Journ. of Clin. Endocrin. & Metab., 46: 604-612 (1978); Roos et al., Journ. of Clin. Endocrin. & Metab., 53: 709-721 (1981); MacGregor et al., Endocrin., 112: 1019-1025 (1983); Hanley et al., Journ. of Clin. Endocrin. & Metab., 63: 1075-1079 (1986); Morrissey et al., Endocrin., 107: 164-171 (1980); MacGregor et al., Journ. of Biol. Chem., 261: 1929-1934 (1986); MacGregor et al., Journ. of Biol. Chem., 254: 4428-4433 (1979); Kubler et al., Experim. & Clin. Endocrin., 88: 101-108 (1986); Schachter et al., Surgery, 110: 1048-1052 (1991); Tanguay et al., Endocrin., 128: 1863-1868 (1991).

Furthermore, it is now apparent that the C-terminal region of PTH has a novel receptor which is specific for this region of the hormone. See, for instance, Hodsman et al., J. Clin. Endocrinol. Metab., 88, pp. 5212-5220 (2003). Accordingly, the full-length PTH has biological properties that are distinct from those of N-terminal PTH analogs.

However, the importance and effects of full length parathyroid hormone on bone growth, calcium physiology, and replenishment are still not readily understood as, maybe, for example, the effects of calcium. The normal daily rise and fall of PTH levels in the blood have a profound effect on bone, and injections of PTH can stimulate the growth of new bone in cases where bone has been lost to osteoporosis.

Hypoparathyroidism is a life-long disease characterized by an inadequate production of parathyroid hormone (PTH) by the parathyroid glands. Because PTH is critical for regulation of calcium and phosphate levels, loss of PTH reduces calcium levels in blood and bones and increases phosphate levels (hypocalcemia and hyperphosphatemia). Hypocalcemia leads to symptoms such as neuromuscular irritability, including paresthesias, muscle twitching, laryngeal spasms (which can lead to inability to speak and to alert health providers to the underlying medical condition, which has led to delayed or incorrect treatment), and possibly tetany and seizures.

Unlike other proteins that have been successfully formulated, PTH is particularly sensitive to various forms of degradation. For example, oxidation can occur at methionine residues at positions 8 and 18, giving rise to the oxidized PTH species ox-M(8)-PTH and ox-M(18)-PTH, while deamidation can occur at asparagine in position 16, giving rise to d16-PTH. The polypeptide chain becomes truncated by breakage of peptide bonds, both at the N- and C-terminals. Furthermore, PTH may also be adsorbed to surfaces, form unspecific aggregates and/or precipitate, thus reducing the available concentration of the drug. All these degradation reactions, and combinations thereof, leads to partial or complete loss of PTH bioactivity. A formulation of PTH must therefore prevent these degradation reactions.

Teriparatide (PTH(1-34) sold by Eli Lilly and Co under the brand name Forteo®) has been identified as an effective alternative to calcitriol therapy for hypoparathyroidism and is able to maintain normal serum calcium levels without hypercalciuria.

A full-length PTH(1-84) has recently been approved as a safe and effective treatment for hypoparathyroidism (sold by Shire-NPS Pharmaceuticals under the brand name NATPARA®). It is the first specific hormone replacement for hypoparathyroidism, and is a once-daily subcutaneous injectable, to be taken as an adjunct to calcium and vitamin D. However, due to a short in vivo half-life, human pharmacokinetic profile of NATPARA exhibits a fast clearance and high peak-trough ratio which results in significant intraday serum calcium fluctuation and poor control of calciuria, a condition associated with elevated calcium levels in the urine.

Thus, there exists a need for improved PTH receptor agonists, particularly those having long-acting activity at the PTH receptor and a more steady-state physiological profile. See Winer K K et al, *J. Clin. Endocrinol. Metab*, 2003, 88(9), 4214-20.

SUMMARY OF THE INVENTION

Various non-limiting aspects and embodiments of the invention are described below.

In one aspect, parathyroid hormone (PTH) variants are provided. In some embodiments, a PTH variant according to the invention may be a PTH-Fc fusion protein comprising PTH, or a variant thereof, chemically linked to an Fc region of a human IgG antibody, or a derivative thereof. In one embodiment, the PTH, or a variant thereof, linked to Fc may be a full-length PTH (i.e., PTH(1-84)), or a truncated PTH, e.g., a C-terminally truncated PTH or a variant thereof. In one embodiment, the PTH linked to Fc may be PTH(1-74), or PTH(1-64), or PTH(1-54), or PTH(1-44). In one embodiment, the PTH linked to Fc is not PTH(1-34). In one embodiment, the PTH linked to Fc may be a full-length PTH(1-84), e.g., a mutated PTH (1-84).

In one embodiment, the PTH linked to Fc may be any length from PTH(1-35) to PTH(1-83). In one embodiment, the PTH linked to Fc may be PTH(1-33).

In one embodiment, the PTH linked to Fc may be PTH (1-84), or PTH(1-83), or PTH(1-82), or PTH(1-81), or PTH(1-80), or PTH(1-79), or PTH(1-78), or PTH(1-77), or PTH(1-76), or PTH(1-75), or PTH(1-74), or PTH(1-73), or PTH(1-72), or PTH(1-71), or PTH(1-70), or PTH(1-69), or PTH(1-68), or PTH(1-67), or PTH(1-66), or PTH(1-65), or PTH(1-64), or PTH(1-63), or PTH(1-62), or PTH(1-61), or PTH(1-60), or PTH(1-59), or PTH(1-58), or PTH(1-57), or PTH(1-56), or PTH(1-55), or PTH(1-54), or PTH(1-53), or PTH(1-52), or PTH(1-51), or PTH(1-50), or PTH(1-49), or PTH(1-48), or PTH(1-47), or PTH(1-46), or PTH(1-45), or PTH(1-44), or PTH(1-43), or PTH(1-42), or PTH(1-41), or PTH(1-40), or PTH(1-39), or PTH(1-38), or PTH(1-37), or PTH(1-36), or PTH(1-35), or PTH(1-33).

In one embodiment, the amino acid sequence of the PTH linked to Fc comprises further modifications selected from amino acid substitution, addition, or deletion. In one embodiment, the PTH linked to Fc comprises a F34A substitution, a F34D substitution, a V35S substitution, or a V35T substitution, or a combination thereof. In one embodiment, the PTH linked to Fc may be further modified, e.g., PEGylated, glycosylated, etc. In one embodiment, the PTH linked to Fc is PEGylated. In one embodiment, the PTH linked to Fc is glycosylated. In one embodiment, the Fc is a native Fc form. In another embodiment, the Fc comprises further modifications selected from amino acid substitution, addition, or deletion. In one embodiment, the Fc is hFcLALA comprising L234A and L235A substitutions. In other embodiments, the Fc may be modified for increased half-life extension, e.g. as described in Yang et al, mAbs, 2017, 9, 1105 and other methods commonly known in the art.

In one embodiment, the Fc-linked PTH variants having the amino acid sequence of SEQ ID NO: 8-11 are provided.

In one embodiment, the Fc-linked PTH variants according to the invention are provided as a divalent structure, i.e., having two copies of PTH and one copy of Fc.

In another embodiment, the Fc-linked PTH variants according to the invention are provided as a monovalent structure, i.e., having one copy of PTH and one copy of Fc. In one embodiment, the monovalent PTH-Fc variants may be prepared using heavy chain mutations known in the art (e.g., knob and hole or the like). One method known in the art is described, e.g., in U.S. Pat. No. 8,679,785. In another embodiment, monovalent PTH-Fc variants may be prepared using a monomeric Fc, where the two Fc moieties may be connected via a linker, e.g., an amino acid linker.

In one embodiment, the serum half-life of the PTH-Fc fusion proteins of the invention is longer than the serum half-life of PTH(1-84). In one embodiment, PTH-Fc fusion proteins of the invention have a serum half-life that is 2-fold longer, or 3-fold longer, or 5-fold longer, or 10-fold longer, or 20-fold longer, or 30-fold longer, or 40-fold longer than the serum half-life of PTH(1-84). In one embodiment, PTH-Fc fusion proteins of the invention have a serum half-life that is 40-fold longer than the serum half-life of PTH(1-84).

In another embodiment, the peak-trough ratio of the PTH-Fc fusion protein is lower than the peak-trough ratio of exogenous PTH(1-84). In one embodiment, PTH-Fc fusion proteins of the invention have a peak-trough ratio that is at least 2-fold lower than the peak-trough ratio of PTH(1-84). In one embodiment, PTH-Fc fusion proteins of the invention have a peak-trough ratio that is at least 10-fold lower than the peak-trough ratio of PTH(1-84).

In some embodiments, the PTH variant is processed from a PTH variant precursor polypeptide that comprises a signal peptide directly linked with the PTH variant. The signal peptide on the polypeptide may promote secretion of the PTH variant from a mammalian host cell used to produce the PTH variant, with the signal peptide cleaved from the PTH variant after secretion. Any number of signal peptides may be used. In one embodiment, the signal peptide may have the following sequence (IgK signal peptide): METPAQLL-FLLLWLPDTTG (SEQ ID NO: 3). In another embodiment, the signal peptide may have the following sequence (IgG heavy chain signal peptide): MEFGLSWLFLVAILKGVQC (SEQ ID NO: 4). In yet another embodiment, the signal peptide may have the following sequence (CD33 signal peptide): MPLLLLLPLLWAGALA (SEQ ID NO: 5). In one particular embodiment, CD33 signal peptide having the sequence MPLLLLLPLLWAGALA (SEQ ID NO: 5) may provide the optimal signal peptide cleavage, leaving position 1 of the PTH variant intact.

In another aspect, a pharmaceutical composition comprising at least one PTH-Fc fusion protein of the invention and a pharmaceutically acceptable carrier is provided.

In another aspect, a pharmaceutical dosage form comprising at least one PTH-Fc fusion protein of the invention or the pharmaceutical composition of the invention is provided. In one embodiment, the pharmaceutical dosage form of the invention is a liquid dosage form. In one embodiment, the pharmaceutical dosage form is suitable for administration by injection or infusion.

In another aspect, a nucleic acid encoding a PTH variant according to the invention is provided. In one embodiment, a nucleic acid encoding a PTH-Fc fusion variant protein is provided.

In another aspect, an expression vector comprising the nucleic acid encoding a PTH variant according to the invention is provided. In one embodiment, an expression vector comprising the nucleic acid encoding a PTH-Fc fusion variant protein is provided.

In another aspect, a host cell comprising an expression vector or a nucleic acid encoding a PTH variant according to the invention is provided. In one embodiment, the host cell comprising an expression vector or a nucleic acid encoding a PTH-Fc fusion variant protein is provided. In one embodiment, the host cell is a prokaryotic cell, a yeast cell, an insect cell, or a mammalian cell. In one embodiment, host cell is a CHO cell.

In another aspect, a method of controlling serum calcium and phosphate levels in a subject in need thereof is provided, the method comprising administering to the subject a PTH variant of the invention, or a pharmaceutical composition comprising a PTH variant of the invention, or a pharmaceutical dosage form comprising a PTH variant of the invention.

In another aspect, a method of controlling urinary calcium levels in a subject in need thereof is provided, the method comprising administering to the subject a PTH variant of the invention, or a pharmaceutical composition comprising a PTH variant of the invention, or a pharmaceutical dosage form comprising a PTH variant of the invention.

In another aspect, a method of treating a subject with hypoparathyroidism is provided, the method comprising administering to the subject an effective amount of a PTH variant of the invention, or a pharmaceutical composition comprising a PTH variant of the invention, or a pharmaceutical dosage form comprising a PTH variant of the invention.

In another aspect, a method of treating a subject with hypoparathyroidism is provided, the method comprising administering to the subject an effective amount of a PTH variant of the invention, or a pharmaceutical composition comprising a PTH variant of the invention, or a pharmaceutical dosage form comprising a PTH variant of the invention.

In some embodiments, the PTH variant of the invention is administered twice a day, or once daily, or every two days, or every three days, or every 5-8 days. In one embodiment, the PTH variant of the invention is administered once daily. In one embodiment, the PTH variant of the invention is administered once weekly. In one embodiment, the PTH variant of the invention is administered subcutaneously.

In some embodiments, the dose of the PTH variant of the invention may need to be titrated for individuals due to variance in the population. In one embodiment, the PTH variant of the invention is administered in an amount from about 1 µg per day to about 500 µg per day, or about 2 µg per day to about 250 µg per day, or about 5 µg per day to about 100 µg per day, or about 10 µg per day to about 80 µg per day, or about 20 µg per day to about 100 µg per day, or about 50 µg per day to about 100 µg per day, or about 50 µg per day, or about 60 µg per day, or about 70 µg per day, or about 80 µg per day, or about 90 µg per day, or about 100 µg per day.

These and other aspects of the present invention will become apparent to those skilled in the art after a reading of the following detailed description of the invention, including the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 13A is a flowchart of the development of the polishing step of PTH-66 purification; FIG. 13B is a flowchart of the process flow.

DETAILED DESCRIPTION

Figure 1:
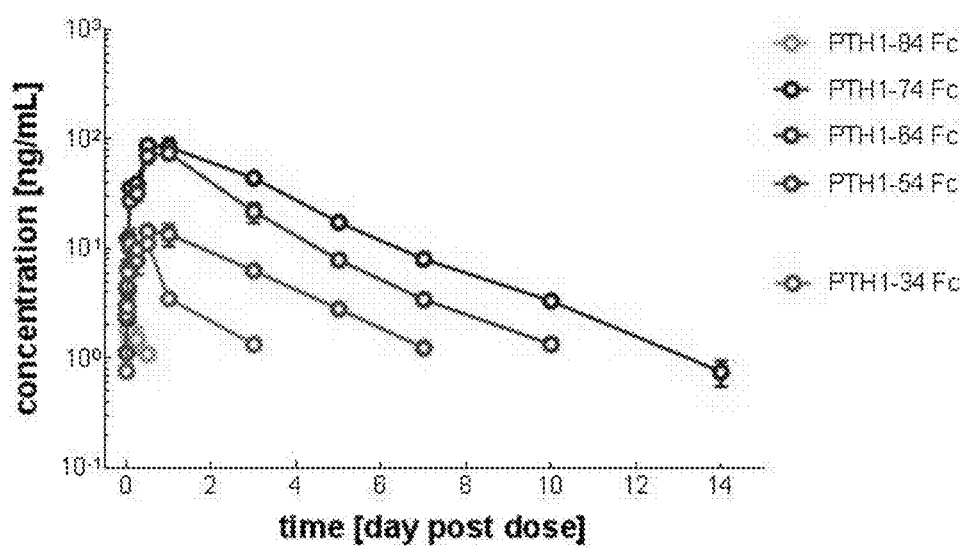
FIG. 1 is a comparison of serum concentrations of different C-terminal truncated PTH-Fc fusion variants as a function of time following single subcutaneous administration to rats.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein, and/or which will become apparent to those persons skilled in the art upon reading this disclosure.

The terms "treat" or "treatment" of a state, disorder, or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

A "subject" or "patient" or "individual" or "animal", as used herein, refers to humans, veterinary animals (e.g., cats, dogs, cows, horses, sheep, pigs, etc.) and experimental animal models of diseases (e.g., mice, rats). In a preferred embodiment, the subject is a human.

As used herein the term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

As used herein, the term "fusion protein" or "chimeric protein" refers to a protein created through the joining of two or more originally separate proteins, or portions thereof. In some embodiments, a linker or spacer will be present between each protein.

As used herein, the term "half-life" is the time required for a quantity such as protein concentration or activity to fall to half of its value as measured at the beginning of a time period.

As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

As used herein, the term "linker" refers to, in a fusion protein, an amino acid sequence other than that appearing at a particular position in the natural protein or a derivative and is generally designed to be flexible or to interpose a structure, such as an α-helix, between two protein moieties. A linker is also referred to as a spacer. A linker or a spacer typically does not have biological function on its own.

The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified. As used herein, the terms "polypeptide" and "peptide" are used inter-changeably. The term "polypeptide" can also refer to proteins.

As used herein, the term "PTH variant" refers to any derivative of native PTH(1-84), including, without limitation, a PTH(1-84) derivative comprising amino acid additions, deletions, and/or substitutions, a truncated (e.g., a C-terminally truncated) PTH(1-84), a PTH fused to a peptide or protein or protein domain, either directly or via a linker or spacer, and a PTH that has been post-translationally modified in any way known in the art (e.g., glycosylated, PEGylated, and the like) or combinations thereof.

PTH

Parathyroid hormone (PTH) is a polypeptide secreted by the mammalian parathyroid gland. The native PTH is 84 amino acids long and has the following sequence (SEQ ID NO: 1):

SVSEIQLMHNLGKHLNSMERVEWLRKKLQDVHNFVALGAPLAPRDAGS

QRPRKKEDNVLVESHEKSLGEADKADVNVLTKAKSQ, or

Ser Val Ser Glu Ile Gln Leu Met His Asn Leu Gly

Lys His Leu Asn Ser Met Glu Arg Val Glu Trp Leu

Arg Lys Lys Leu Gln Asp Val His Asn Phe Val Ala

Leu Gly Ala Pro Leu Ala Pro Arg Asp Ala Gly Ser

Gln Arg Pro Arg Lys Lys Glu Asp Asn Val Leu Val

Glu Ser His Glu Lys Ser Leu Gly Glu Ala Asp Lys

Ala Asp Val Asn Val Leu Thr Lys Ala Lys Ser Gln

As used herein, the terms "human PTH" or "hPTH" are encompassed by the terms PTH or parathyroid hormone. Human PTH can be synthesized in vivo, recombinantly (in a cell), or synthetically using standard techniques known in the art.

PTH-Fc Fusions

In some embodiments, PTH variants of the invention are PTH-Fc fusion proteins. "Fc," as used herein, means the Fc region of a human IgG antibody. Fc-Fusion proteins (also known as Fc chimeric fusion protein, Fc-Ig, Ig-based Chimeric Fusion protein and Fc-tag protein) are composed of the Fc domain of IgG chemically linked to a peptide or protein of interest (e.g., PTH).

Fc domains from any IgG may be used. By way of a non-limiting example, Fc domains of IgG1, or IgG2, or IgG3, or IgG4 may be used, as well as various combinations of Fc domains originating from different IgGs, such as, e.g., half IgG2 and half IgG4. In one non-limiting embodiment, PTH-Fc fusion proteins of the invention have Fc domains of a human IgG1 antibody.

Silenced effector functions can be obtained by mutation in the Fc region of the antibodies, and different IgGs may have different silencer regions known to those of skill in the art. For example, for IgG1 the following silencer regions are known and have been described in the art: LALA and N297A (Strohl, W., 2009, Curr. Opin. Biotechnol. vol. 20(6):685-691); and D265A (Baudino et al., 2008, J. Immunol. 181: 6664-69; Strohl, W., supra). Examples of silent Fc IgG1 antibodies comprise the so-called LALA mutant ("hFcLALA") comprising L234A and L235A (EU numbering) mutation in the IgG1 Fc amino acid sequence. Another example of a silent IgG1 antibody comprises the D265A mutation. Another silent IgG1 antibody comprises the N297A mutation, which results in aglycosylated/non-glycosylated antibodies.

As used herein, IgG1 hFcLALA has the following sequence, with the LALA mutation underlined (SEQ ID NO: 2):

DKTHTCPPCPAPE<u>AA</u>GGPSVFLFPPKPKDTLMISRTPEVTCVVVDVSH

EDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVS

LTCLVKGFYPSDIAVEWESNGQPENNYKTTPPVLDSDGSFFLYSKLTV

DKSRWQQGNVFSCSVMHEALHNHYTQKSLSLSPG

The PTH sequence may be directly or indirectly linked to an Fc domain. In one embodiment, PTH is linked to an Fc domain directly. In other embodiments, PTH is linked to an Fc domain by an amino acid linker.

In some embodiments, the Fc region may be further modified to further extend the half-life of the fusion protein. In one non-limiting example, half-life extension technology, e.g. NHance technology by ArGenX, may be utilized in combination with the PTH-Fc variants of the invention. The NHance technology is described, e.g., in U.S. Pat. No. 8,163,881, the contents of which are incorporated by reference herein in their entirety.

In one embodiment, the Fc-linked PTH variants according to the invention are provided as a divalent structure, i.e., having two copies of PTH and one copy of Fc.

In another embodiment, the Fc-linked PTH variants according to the invention are provided as a monovalent structure, i.e., having one copy of PTH and one copy of Fc. In one embodiment, the monovalent PTH-Fc variants may be prepared using heavy chain mutations known in the art (e.g., knob and hole or the like). One method known in the art is described, e.g., in U.S. Pat. No. 8,679,785. In another embodiment, monovalent PTH-Fc variants may be prepared using a monomeric Fc, where the two Fc moieties may be connected via a linker, e.g., an amino acid linker.

Signal Peptides and Protease Tags

In some embodiments, PTH variants of the invention are processed from a PTH variant precursor polypeptide that comprises a signal peptide directly linked with the PTH variant. The signal peptide on the polypeptide may promote secretion of the PTH variant from a mammalian host cell used to produce the PTH variant, with the signal peptide cleaved from the PTH variant after secretion. Any number of signal peptides may be used.

In some embodiments, an IgK leader sequence is present in the variants of the invention, having the following sequence (SEQ ID NO: 3):

METPAQLLFLLLLWLPDTTG.

In some embodiments, an IgG heavy chain signal peptide is present in the variants of the invention, having the following sequence (SEQ ID NO: 4):

MEFGLSWLFLVAILKGVQC.

In some embodiments, a CD33 signal peptide is present in the variants of the invention, having the following sequence (SEQ ID NO: 5):

MPLLLLLPLLWAGALA.

In one particular embodiment, CD33 signal peptide having the sequence MPLLLLLPLLWAGALA (SEQ ID NO: 5) may provide the optimal signal peptide cleavage, leaving position 1 of the PTH variant intact.

In some embodiments, poly-histidine tags (HIS tags) are present in the variants of the invention for ease of PTH protein purification using affinity chromatography resins that recognize and bind to the HIS tag. In one embodiment, a TEV-HIS tag is present at the C-terminus of the PTH variants of the invention. The TEV component is a protease recognition site that allows for removal of the HIS tag after protein purification. In one embodiment, the sequence of the TEV-HIS tag is ENLYFQSHHHHHH (SEQ ID NO: 6). In one embodiment, part of the TEV recognition sequence, ENLYFQ (SEQ ID NO: 7), remains on the terminus of the protein and does not affect the activity of the protein.

Protein Glycosylation

Glycosylation, as used herein, is a reaction in which a carbohydrate (a glycan) is attached to a peptide or a protein. Different classes of glycans are recognized, in which the two most prominent are: N-linked glycans attached to a nitrogen or arginine side chains and O-linked glycans attached to the hydroxyl oxygen of serine, threonine, tyrosine, hydroxylysine, or hydroxyproline side chains.

In some embodiments, amino acid substitutions to insert a glycosylation site are introduced into PTH variants of the invention. In some embodiments, these amino acid substitutions may introduce a serine moiety into the PTH variant. In some embodiments, PTH variants of the invention may comprise a F34A, F34D, and/or a V35S, or V35T mutation to insert a glycan site into the PTH variant.

In some embodiments, amino acid changes may be made at F34 (e.g., F34A or F34D) and/or V35 (e.g., V35S or V35T) to minimize proteolysis observed in this area during expression of the molecules in particular cell types, e.g., CHO cells. F34A and F34D mutations reduce proteolysis. The combination of F34A and V35S (or V35T) mutations reduces proteolysis to an even greater degree. These mutations create a consensus N-linked glycosylation site, which includes position N33. This results in glycosylation at position N33 which greatly reduces proteolysis in this location.

In some embodiments insertion of the glycan site at N33 reduces protein cleavage during host cell expression. Glycans introduce additional size and bulk to the PTH variants. Glycan sites may also improve solubility of the PTH variants. Glycan sites may also extend the half-life (T1/2) of the PTH variants. Glycan insertion at the site of protein mutation may also reduce potential immunogenicity of the mutated sequence. In some embodiments, amino acid substitution to insert a glycosylation site may be combined with other mutations or sequence truncations or posttranslational modification for the PTH variant.

In some embodiments, amino acid changes may be made at L59 (e.g., L59S or L59T). This mutation creates a glycosylation site at position N57, which may reduce protein cleavage during host cell expression.

Other variants: In some embodiments, amino acid substitutions are introduced into PTH variants improve developability characteristics. In some embodiments, these amino acid substitutions result in reduced cleavage of the PTH variants during expression. In some embodiments, these amino acid substitutions result in improved solubility of the PTH variants. In some embodiments, these amino acid substitutions result in glycan insertion. In some embodiments, these amino acid substitutions may introduce an aspartate into the sequence.

In some embodiments, PTH variants of the invention may comprise a F34D mutation to decrease protein cleavage during expression. In some embodiments, PTH variants containing F34D may be combined with other mutations or sequence truncations or posttranslational modifications for the PTH variant.

Typically, a suitable PTH variant has an in vivo half-life of or greater than about 2 hours, 3 hours, 4 hours, 6 hours, 8 hours, 10 hours, 12 hours, 14 hours, 16 hours, 18 hours, 20 hours, 22 hours, 24 hours, 26 hours, 28 hours, 30 hours, 32 hours, 34 hours, 36 hours, 38 hours, 40 hours, 42 hours, 44 hours, 46 hours, or 48 hours. In some embodiments, a PTH variant has an in vivo half-life of between 2 and 48 hours, between 2 and 44 hours, between 2 and 40 hours, between 3 and 36 hours, between 3 and 32 hours, between 3 and 28 hours, between 4 and 24 hours, between 6 and 24 hours, and between 6 and 18 hours.

Listing of Select Parathyroid Hormone Variants

In the below listing and throughout the specification, the following abbreviations are used:

PTH(1-N) means parathyroid hormone peptide residues 1 through N, where N can be 84 (for native length PTH and variants) or less than 84 (for C-terminal truncated PTH variants). For example, PTH(1-84) means parathyroid hormone peptide residues 1 through 84 (full-length sequence); PTH(1-74) means parathyroid hormone peptide residues 1 through 74, i.e., C-terminal truncated variant of PTH(1-84) which is the first 74 residues of PTH, with the last 10 residues having been removed; PTH(1-34) means parathyroid hormone peptide residues 1 through 34, (i.e., C-terminal truncated variant of PTH(1-84) which is the first 34 residues with the last 50 residues having been removed, etc.

Point mutation in the variant sequences are designated according to the standard convention; e.g., F34A means the phenylalanine amino acid in position 34 is replaced by an alanine amino acid; F34D means that the phenylalanine amino acid in position 34 is replaced by an aspartate residue, V35S means the valine in position 35 is replaced by a serine, etc.

Δ means [deleted sequence], e.g., ΔLys means removal of a lysine residue. For constructs contained here, the Lys removed is the C-terminal region of the Fc molecule to, inter alia, improve homogeneity of the drug product.

In one embodiment, the PTH linked to Fc may be a full-length PTH(1-84), e.g., a mutated PTH(1-84).

In one embodiment, the PTH linked to Fc may be a truncated PTH of any length from PTH(1-35) to PTH(1-83). In one embodiment, the PTH linked to Fc may be PTH(1-33).

In some embodiments of the invention, the PTH linked to Fc may be PTH(1-84), or PTH(1-83), or PTH(1-82), or PTH(1-81), or PTH(1-80), or PTH(1-79), or PTH(1-78), or PTH(1-77), or PTH(1-76), or PTH(1-75), or PTH(1-74), or PTH(1-73), or PTH(1-72), or PTH(1-71), or PTH(1-70), or PTH(1-69), or PTH(1-68), or PTH(1-67), or PTH(1-66), or PTH(1-65), or PTH(1-64), or PTH(1-63), or PTH(1-62), or PTH(1-61), or PTH(1-60), or PTH(1-59), or PTH(1-58), or PTH(1-57), or PTH(1-56), or PTH(1-55), or PTH(1-54), or PTH(1-53), or PTH(1-52), or PTH(1-51), or PTH(1-50), or PTH(1-49), or PTH(1-48), or PTH(1-47), or PTH(1-46), or PTH(1-45), or PTH(1-44), or PTH(1-43), or PTH(1-42), or PTH(1-41), or PTH(1-40), or PTH(1-39), or PTH(1-38), or PTH(1-37), or PTH(1-36), or PTH(1-35), or PTH(1-33).

In the below descriptions of exemplary embodiments of the invention the signal peptide is marked in italics, the PTH region is bolded, with any mutations therein underlined, and any fusion sequence is marked by a wave underline.

Molecule designation 'PTH-66' (SEQ ID NO: 8)
Description: PTH(1-74)-[F34A, V35S]-hFcLALA-ΔLys
*Signal peptide*, PTH1-74, mutations to insert glycan site, Fc

*METPAQLLFLLLLWLPDTTG*SVSEIQLMHNLGKHLNSMERVEWLRKKL

QDVHNASALGAPLAPRDAGSQRPRKKEDNVLVESHEKSLGEADKADDKTHTCPPCP

APEAAGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPG

Molecule designation 'PTH-67' (SEQ ID NO: 9)
Description: PTH(1-64)-[F34A, V35S]-hFcLALA-ΔLys
*Signal peptide*, PTH1-64, mutations to insert glycan site, Fc

*METPAQLLFLLLLWLPDTTG*SVSEIQLMHNLGKHLNSMERVEWLRKKL

QDVHNASALGAPLAPRDAGSQRPRKKEDNVLVESHEDKTHTCPPCPAPEAAGGPSVF

LFPPKPKDTLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSKLTVDKSRW

QQGNVFSCSVMHEALHNHYTQKSLSLSPG

Molecule designation 'PTH-68' (SEQ ID NO: 10)
Description: PTH(1-54)-[F34A, V35S]-hFcLALA-ΔLys
*Signal peptide*, PTH1-54, mutations to insert glycan site, Fc

*METPAQLLFLLLLWLPDTTG*SVSEIQLMHNLGKHLNSMERVEWLRKKL

QDVHNASALGAPLAPRDAGSQRPRKKDKTHTCPPCPAPEAAGGPSVFLFPPKPKDTL

MISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSV

MHEALHNHYTQKSLSLSPG

Molecule designation 'PTH-69' (SEQ ID NO: 11)
Description: PTH(1-44)-[F34A, V35]-hFcLALA-ΔLys
*Signal peptide*, PTH1-44, mutations to insert glycan site, Fc

*MEPTAQLLFLLLLWLPDTTG*SVSEIQLMHNLGKHLNSMERVEWLRRL

QDVHNASALGAPLAPRDKTHTCPPCPAPEAAGGPSVFLFPPKPKDTLMISRTPEVTCVV

VDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMHEALHNHYT

QKSLSLSPG

Molecule designation 'PTH-11' (SEQ ID NO: 12)
Description: PTH(1-84)-hFcLALA
*METPAQLLFLLLLWLPDTTG*SVSEIQLMHNLGKHLNSMERVEWLRKKL

```
                        -continued
QDVHNASALGAPLAPRDAGSQRPRKKEDNVLVESHEKSLGEADKADVNLTKAKSQ

DKTHTCPPCPAPEAAGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG
```

Other PTH Variants

In one embodiment, PTH variants according to the invention may be conjugated, directly or via a linker, to albumin, or a domain of albumin. In one embodiment, PTH-albumin fusions according to the invention may be prepared by methods described in U.S. Pat. No. 7,592,010. The PTH-albumin variants may be monovalent structures, i.e., having one copy of PTH and one copy of albumin or a domain of albumin. In one embodiment, the serum half-life of the PTH-albumin fusion proteins is longer than the serum half-life of PTH(1-84). In one embodiment, PTH-albumin fusion proteins of the invention have a serum half-life that is 2-fold longer, or 3-fold longer, or 5-fold longer, or 10-fold longer, or 20-fold longer, or 30-fold longer, or 40-fold longer than the serum half-life of PTH(1-84). In one embodiment, PTH-Fc fusion proteins of the invention have a serum half-life that is 40-fold longer than the serum half-life of PTH(1-84).

In one embodiment, the PTH linked to albumin may be mutated PTH(1-84), or PTH(1-83), or PTH(1-82), or PTH(1-81), or PTH(1-80), or PTH(1-79), or PTH(1-78), or PTH(1-77), or PTH(1-76), or PTH(1-75), or PTH(1-74), or PTH(1-73), or PTH(1-72), or PTH(1-71), or PTH(1-70), or PTH(1-69), or PTH(1-68), or PTH(1-67), or PTH(1-66), or PTH(1-65), or PTH(1-64), or PTH(1-63), or PTH(1-62), or PTH(1-61), or PTH(1-60), or PTH(1-59), or PTH(1-58), or PTH(1-57), or PTH(1-56), or PTH(1-55), or PTH(1-54), or PTH(1-53), or PTH(1-52), or PTH(1-51), or PTH(1-50), or PTH(1-49), or PTH(1-48), or PTH(1-47), or PTH(1-46), or PTH(1-45), or PTH(1-44), or PTH(1-43), or PTH(1-42), or PTH(1-41), or PTH(1-40), or PTH(1-39), or PTH(1-38), or PTH(1-37), or PTH(1-36), or PTH(1-35), or PTH(1-33).

Nucleic Acids

In another aspect a nucleic acid is provided comprising a sequence encoding the PTH variants described herein. The sequence may have 70%, 75%, 80%, 85%, 90%, 91%, 92%, 93%, 94%, 95%, 96%, 97%, 98%, 99% or 100% identity to any of SEQ ID NOS: 8-12. In some embodiments, the nucleic acid may comprise further noncoding sequence. The nucleic acids may further comprise specified fragments, variants or consensus sequences thereof, or a deposited vector comprising at least one of these sequences. The nucleic acid molecules can be in the form of RNA, such as mRNA, hnRNA, tRNA or any other form, or in the form of DNA, including, but not limited to, cDNA and genomic DNA obtained by cloning, produced synthetically, via gene therapy, e.g., using AAV, or any combination thereof. The DNA can be triple-stranded, double-stranded or single-stranded, or any combination thereof. Any portion of at least one strand of the DNA or RNA can be the coding strand, also known as the sense strand, or it can be the noncoding strand, also referred to as the antisense strand.

In some embodiments, the nucleic acid encoding a transgene may be modified to provide increased expression of the encoded PTH variant, which is also referred to as codon optimization. For example, the nucleic acid encoding a transgene can be modified by altering the open reading frame for the coding sequence. As used herein, the term "open reading frame" is synonymous with "ORF" and means any nucleotide sequence that is potentially able to encode a protein, or a portion of a protein. An open reading frame usually begins with a start codon (represented as, e.g. AUG for an RNA molecule and ATG in a DNA molecule in the standard code) and is read in codon-triplets until the frame ends with a STOP codon (represented as, e.g. UAA, UGA or UAG for an RNA molecule and TAA, TGA or TAG in a DNA molecule in the standard code). As used herein, the term "codon" means a sequence of three nucleotides in a nucleic acid molecule that specifies a particular amino acid during protein synthesis; also called a triplet or codon-triplet. For example, of the 64 possible codons in the standard genetic code, two codons, GAA and GAG encode the amino acid glutamine whereas the codons AAA and AAG specify the amino acid lysine. In the standard genetic code three codons are stop codons, which do not specify an amino acid. As used herein, the term "synonymous codon" means any and all of the codons that code for a single amino acid. Except for methionine and tryptophan, amino acids are coded by two to six synonymous codons. For example, in the standard genetic code the four synonymous codons that code for the amino acid alanine are GCA, GCC, GCG and GCU, the two synonymous codons that specify glutamine are GAA and GAG and the two synonymous codons that encode lysine are AAA and AAG.

A nucleic acid encoding the open reading frame of a PTH variant may be modified using standard codon optimization methods. Various commercial algorithms for codon optimization are available and can be used to practice the present invention. Typically, codon optimization does not alter the encoded amino acid sequences.

A nucleotide change may alter a synonymous codon within the open reading frame in order to agree with the endogenous codon usage found in a particular heterologous cell selected to express a PTH variant. Alternatively, or additionally, a nucleotide change may alter the G+C content within the open reading frame to better match the average G+C content of open reading frames found in endogenous nucleic acid sequence present in the heterologous host cell. A nucleotide change may also alter a polymononucleotide region or an internal regulatory or structural site found within a PTH variant sequence. Thus, a variety of modified or optimized nucleotide sequences are envisioned including, without limitation, nucleic acid sequences providing increased expression of PTH variants in a prokaryotic cell, yeast cell, insect cell, and in a mammalian cell.

As indicated herein, polynucleotides may further include additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding a PTH variant or specified portion can be fused to a marker sequence, such as a sequence encoding a peptide that facilitates purification of the fused PTH variant or specified portion comprising a PTH variant fragment or portion.

The nucleic acids may further comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

The coding region of a transgene may include one or more silent mutations to optimize codon usage for a particular cell type. For example, the codons of a PTH variant may be optimized for expression in a vertebrate cell. In some embodiments, the codons of a PTH variant may be optimized for expression in a mammalian cell. In some embodiments, the codons of a PTH variant may be optimized for expression in a human cell. In some embodiments, the codons of a PTH variant may be optimized for expression in a CHO cell.

A nucleic acid sequence encoding a PTH variant as described in the present application, can be molecularly cloned (inserted) into a suitable vector for propagation or expression in a host cell, or an entire plasmid may be synthesized as well in some embodiments. For example, the PTH variant sequences comprising a signal peptide effective to secrete the PTH variant from the host cell are inserted into the suitable vector, such as sequences selected from SEQ ID NOS: 8-12. A wide variety of expression vectors can be used to practice the present invention, including, without limitation, a prokaryotic expression vector; a yeast expression vector; an insect expression vector and a mammalian expression vector. Exemplary vectors suitable for the present invention include, but are not limited to, viral based vectors (e.g., AAV based vectors, retrovirus based vectors, plasmid based vectors). In some embodiments, a nucleic acid sequence encoding a PTH variant can be inserted into a suitable vector. Typically, a nucleic acid encoding a PTH variant is operably linked to various regulatory sequences or elements.

Various regulatory sequences or elements may be incorporated in an expression vector suitable for the present invention. Exemplary regulatory sequences or elements include, but are not limited to, promoters, enhancers, repressors or suppressors, 5' untranslated (or non-coding) sequences, introns, 3' untranslated (or non-coding) sequences.

As used herein, a "promoter" or "promoter sequence" is a DNA regulatory region capable of binding an RNA polymerase in a cell (e.g., directly or through other promoter bound proteins or substances) and initiating transcription of a coding sequence. A promoter sequence is, in general, bound at its 3' terminus by the transcription initiation site and extends upstream (5' direction) to include the minimum number of bases or elements necessary to initiate transcription at any level. The promoter may be operably associated with or operably linked to the expression control sequences, including enhancer and repressor sequences or with a nucleic acid to be expressed. In some embodiments, the promoter may be inducible. In some embodiments, the inducible promoter may be unidirectional or bi-directional. In some embodiments, the promoter may be a constitutive promoter. In some embodiments, the promoter can be a hybrid promoter, in which the sequence containing the transcriptional regulatory region is obtained from one source and the sequence containing the transcription initiation region is obtained from a second source. Systems for linking control elements to coding sequence within a transgene are well known in the art (general molecular biological and recombinant DNA techniques are described in Sambrook, Fritsch, and Maniatis, *Molecular Cloning: A Laboratory Manual*, Second Edition, Cold Spring Harbor Laboratory Press, Cold Spring Harbor, N.Y., 1989, which is incorporated herein by reference). Commercial vectors suitable for inserting a transgene for expression in various host cells under a variety of growth and induction conditions are also well known in the art.

In some embodiments, a specific promoter may be used to control expression of the transgene in a mammalian host cell such as, but are not limited to, SRa-promoter (Takebe et al., Molec. and Cell. Bio. 8:466-472 (1988)), the human CMV immediate early promoter (Boshart et al., Cell 41:521-530 (1985); Foecking et al., Gene 45:101-105 (1986)), human CMV promoter, the human CMV5 promoter, the murine CMV immediate early promoter, the EF1-α-promoter, a hybrid CMV promoter for liver specific expression (e.g., made by conjugating CMV immediate early promoter with the transcriptional promoter elements of either human α-1-antitrypsin (HAT) or albumin (HAL) promoter), or promoters for hepatoma specific expression (e.g., wherein the transcriptional promoter elements of either human albumin (HAL; about 1000 bp) or human α-1-antitrypsin (HAT, about 2000 bp) are combined with a 145 long enhancer element of human α-1-microglobulin and bikunin precursor gene (AMBP); HAL-AMBP and HAT-AMBP); the SV40 early promoter region (Benoist at al., Nature 290:304-310 (1981)), the *Orgyia pseudotsugata* immediate early promoter, the herpes thymidine kinase promoter (Wagner at al., Proc. Natl. Acad. Sci. USA 78:1441-1445 (1981)); or the regulatory sequences of the metallothionein gene (Brinster et al., Nature 296:39-42 (1982)). In some embodiments, the mammalian promoter is a is a constitutive promoter such as, but not limited to, the hypoxanthine phosphoribosyl transferase (HPTR) promoter, the adenosine deaminase promoter, the pyruvate kinase promoter, the beta-actin promoter as well as other constitutive promoters known to those of ordinary skill in the art.

In some embodiments, a specific promoter may be used to control expression of a transgene in a prokaryotic host cell such as, but are not limited to, the β-lactamase promoter (Villa-Komaroff et al., Proc. Natl. Acad. Sci. USA 75:3727-3731 (1978)); the tac promoter (DeBoer et al., Proc. Natl. Acad. Sci. USA 80:21-25 (1983)); the T7 promoter, the T3 promoter, the M13 promoter or the M16 promoter; in a yeast host cell such as, but are not limited to, the GAL1, GAL4 or GAL10 promoter, the ADH (alcohol dehydrogenase) promoter, PGK (phosphoglycerol kinase) promoter, alkaline phosphatase promoter, glyceraldehyde-3-phosphate dehydrogenase III (TDH3) promoter, glyceraldehyde-3-phosphate dehydrogenase II (TDH2) promoter, glyceraldehyde-3-phosphate dehydrogenase I (TDH1) promoter, pyruvate kinase (PYK), enolase (ENO), or triose phosphate isomerase (TPI).

In some embodiments, the promoter may be a viral promoter, many of which are able to regulate expression of a transgene in several host cell types, including mammalian cells. Viral promoters that have been shown to drive constitutive expression of coding sequences in eukaryotic cells include, for example, simian virus promoters, herpes simplex virus promoters, papilloma virus promoters, adenovirus promoters, human immunodeficiency virus (HIV) promoters, Rous sarcoma virus promoters, cytomegalovirus (CMV) promoters, the long terminal repeats (LTRs) of Moloney murine leukemia virus and other retroviruses, the thymidine kinase promoter of herpes simplex virus as well as other viral promoters known to those of ordinary skill in the art.

In some embodiments, the gene control elements of an expression vector may also include 5' non-transcribing and 5' non-translating sequences involved with the initiation of transcription and translation, respectively, such as a TATA box, capping sequence, CAAT sequence, Kozak sequence and the like. Enhancer elements can optionally be used to increase expression levels of a polypeptide or protein to be expressed. Examples of enhancer elements that have been shown to function in mammalian cells include the SV40 early gene enhancer, as described in Dijkema et al., EMBO J. (1985) 4: 761 and the enhancer/promoter derived from the long terminal repeat (LTR) of the Rous Sarcoma Virus (RSV), as described in Gorman et al., Proc. Natl. Acad. Sci. USA (1982b) 79:6777 and human cytomegalovirus, as described in Boshart et al., Cell (1985) 41:521. Genetic control elements of an expression vector will also include 3' non-transcribing and 3' non-translating sequences involved with the termination of transcription and translation. Respectively, such as a poly polyadenylation (polyA) signal for stabilization and processing of the 3' end of an mRNA transcribed from the promoter. Exemplary polyA signals include, for example, the rabbit beta globin polyA signal, bovine growth hormone polyA signal, chicken beta globin terminator/polyA signal, and SV40 late polyA region.

Expression vectors will preferably but optionally include at least one selectable marker. In some embodiments, the selectable maker is a nucleic acid sequence encoding a resistance gene operably linked to one or more genetic regulatory elements, to bestow upon the host cell the ability to maintain viability when grown in the presence of a cytotoxic chemical and/or drug. In some embodiments, a selectable agent may be used to maintain retention of the expression vector within the host cell. In some embodiments, the selectable agent is may be used to prevent modification (i.e. methylation) and/or silencing of the transgene sequence within the expression vector. In some embodiments, a selectable agent is used to maintain episomal expression of the vector within the host cell. In some embodiments, the selectable agent is used to promote stable integration of the transgene sequence into the host cell genome. In some embodiments, an agent and/or resistance gene may include, but is not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), zeomycin, mycophenolic acid, or glutamine synthetase (GS, U.S. Pat. Nos. 5,122,464; 5,770,359; 5,827,739) for eukaryotic host cell; tetracycline, ampicillin, kanamycin or chlorampenichol for a prokaryotic host cell; and URA3, LEU2, HIS3, LYS2, HIS4, ADE8, CUP1 or TRP1 for a yeast host cell.

Expression vectors may be transfected, transformed or transduced into a host cell. As used herein, the terms "transfection," "transformation" and "transduction" all refer to the introduction of an exogenous nucleic acid sequence into a host cell. In some embodiments, expression vectors containing nucleic acid sequences encoding for a PTH Fc fusion are transfected, transformed or transduced into a host cell at the same time. In some embodiments, expression vectors containing nucleic acid sequences encoding for a PTH variant are transfected, transformed or transduced into a host cell sequentially.

Examples of transformation, transfection and transduction methods, which are well known in the art, include liposome delivery, i.e., Lipofectamine™ (Gibco BRL) Method of Hawley-Nelson, Focus 15:73 (1193), electroporation, $CaPO_4$ delivery method of Graham and van der Erb, Virology, 52:456-457 (1978), DEAE-Dextran medicated delivery, microinjection, biolistic particle delivery, polybrene mediated delivery, cationic mediated lipid delivery, transduction, and viral infection, such as, e.g., retrovirus, lentivirus, adenovirus adeno-associated virus and Baculovirus (Insect cells).

Once introduced inside cells, expression vectors may be integrated stably in the genome or exist as extra-chromosomal constructs. Vectors may also be amplified, and multiple copies may exist or be integrated in the genome. In some embodiments, cells of the invention may contain 1, 2, 3, 4, 5, 6, 7, 8, 9, 10, 15, 20 or more copies of nucleic acids encoding a PTH variant.

Host Cells

In another aspect is provided a host cell comprising the polynucleotides described herein, e.g., those that allow for expression of a PTH variant in the host cell. The host cell may be a mammalian cell, with non-limiting examples including a BALB/c mouse myeloma line (NSO/l, ECACC No: 85110503); human retinoblasts (PER.C6, CruCell, Leiden, The Netherlands); a monkey kidney CV1 line transformed by SV40 (COS-7, ATCC CRL 1651); a human embryonic kidney line (HEK293 or 293 cells subcloned for growth in suspension culture, Graham et al., J. Gen Virol., 36:59, 1977); a human fibrosarcoma cell line (e.g., HT1080); baby hamster kidney cells (BHK21, ATCC CCL 10); Chinese hamster ovary cells (CHO, Urlaub and Chasin, Proc. Natl. Acad. Sci. USA, 77:4216, 1980), including CHO EBNA (Daramola O. et al., Biotechnol. Prog., 2014, 30(1): 132-41) and CHO GS (Fan L. et al., Biotechnol. Bioeng. 2012, 109(4):1007-15; mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2). In one embodiment, the host cell may be a Chinese hamster ovary cell.

The polynucleotide may in an expression plasmid. The expression plasmid may have any number of origins of replication known to those of ordinary skill in the art. The polynucleotide or expression plasmid may be introduced into the host cell by any number of ways known to those of ordinary skill in the art. For example, a flow electroporation system, such as the MaxCyte GT®, MaxCyte VLX®, or MaxCyte STX® transfection systems, can be used to introduce the polynucleotide or expression plasmid into the host cell.

In various embodiments, the host cell expresses the nucleic acid. The host cell may express PTH variants at a level sufficient for fed-batch cell culture scale or other large scale. Alternative methods to produce recombinant PTH variants at a large scale include roller bottle cultures, bioreactor batch cultures, and perfusion methods. In some embodiments, a recombinant PTH variant protein is produced by cells cultured in suspense. In some embodiments, a recombinant PTH variant protein is produced by adherent cells.

Production

A recombinant PTH variant may be produced by any available means. For example, a recombinant PTH variant may be recombinantly produced by utilizing a host cell system engineered to express a recombinant PTH variant-encoding nucleic acid. Alternatively, or additionally, a recombinant PTH variant may be produced by activating endogenous genes. Alternatively, or additionally, a recombinant PTH variant may be partially or fully prepared by chemical synthesis. Alternatively, a recombinant PTH variant can be produced in vivo by mRNA therapeutics or AAV/lentiviral gene therapy.

In some embodiments, recombinant PTH variants are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (HEK293 or 293 cells subcloned for growth in suspension culture, Graham et al., J. Gen Virol., 36:59, 1977); human fibrosarcoma cell line (e.g., HT1080); baby hamster kidney cells (BHK21, ATCC CCL 10); Chinese hamster ovary cells +/−DHFR (CHO, Urlaub and Chasin, Proc. Natl. Acad. Sci. USA, 77:4216, 1980), including CHO EBNA (Daramola O. et al., Biotechnol. Prog., 2014, 30(1):132-41) and CHO GS (Fan L. et al., Biotechnol. Bioeng. 2012, 109(4):1007-15; mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, recombinant PTH variants are produced from human cells. In some embodiments, recombinant PTH variants are produced from CHO cells or HT1080 cells.

In certain embodiments, a host cell is selected for generating a cell line based on certain preferable attributes or growth under particular conditions chosen for culturing cells. It will be appreciated by one skilled in the art, such attributes may be ascertained based on known characteristic and/or traits of an established line (i.e. a characterized commercially available cell line) or though empirical evaluation. In some embodiments, a cell line may be selected for its ability to grow on a feeder layer of cells. In some embodiments, a cell line may be selected for its ability to grow in suspension. In some embodiments, a cell line may be selected for its ability to grow as an adherent monolayer of cells. In some embodiments a cell line may be chosen for preferential post translational modifications (e.g., glycosylation). In some embodiments, such cells can be used with any tissue culture vessel or any vessel treated with a suitable adhesion substrate. In some embodiments, a suitable adhesion substrate is selected from the group consisting of collagen (e.g. collagen I, II, II, or IV), gelatin, fibronectin, laminin, vitronectin, fibrinogen, BD Matrigel™, basement membrane matrix, dermatan sulfate proteoglycan, Poly-D-Lysine and/or combinations thereof. In some embodiments, an adherent host cell may be selected and modified under specific growth conditions to grow in suspension. Such methods of modifying an adherent cell to grown in suspension are known in the art. For example, a cell may be conditioned to grow in suspension culture, by gradually removing animal serum from the growth media over time.

Typically, cells that are engineered to express a recombinant PTH variant may comprise a transgene that encodes a recombinant PTH variant described herein. It should be appreciated that the nucleic acids encoding recombinant PTH variants may contain regulatory sequences, gene control sequences, promoters, non-coding sequences and/or other appropriate sequences for expressing the recombinant PTH variant. Typically, the coding region is operably linked with one or more of these nucleic acid components.

In some embodiments PTH variants are expressed using a batch culture method. In some embodiments batch culture duration may be for 7-14 days. In some embodiments the batch culture may be for 14-21 days. In some embodiments PTH variants are expressed using a perfusion culture method (collection of culture medium over time each day). In some embodiments, PTH variants are expressed using a pseudoperfusion culture method (daily collection of culture medium at a single time point with replacement with fresh medium). In some embodiments specific feeding regimens/media may be used to promote optimal PTH variant production (improved glycan, reduce clipping). In some embodiments the cell density may be controlled/maintained to promote optimal PTH variant production (improved glycan/reduced clipping).

In some embodiments, a recombinant PTH variant is produced in vivo by mRNA therapeutics. An mRNA encoding for a PTH variant is prepared and administered to a patient in need of the PTH variant. The mRNA can comprise a sequence corresponding to the DNA sequences of SEQ ID NOS: 8-12. Various routes of administration may be used, such as injection, nebulization in the lungs, and electroporation under the skin. The mRNA may be encapsulated in a viral vector or a nonviral vector. Exemplary nonviral vectors include liposomes, cationic polymers and cubosomes.

Recovery and Purification

Various means for purifying the PTH variants from the cells may be used. Various methods may be used to purify or isolate PTH variants produced according to various methods described herein. In some embodiments, the expressed protein is secreted into the medium and thus cells and other solids may be removed, as by centrifugation or filtering for example, as a first step in the purification process. Alternatively, or additionally, the expressed protein is bound to the surface of the host cell. In this embodiment, the host cells expressing the polypeptide or protein are lysed for purification. Lysis of mammalian host cells can be achieved by any number of means well known to those of ordinary skill in the art, including physical disruption by glass beads, utilizing detergents, and exposure to high pH conditions. In some embodiments, PTH variants may be expressed into insoluble fractions (inclusion body). In such embodiments the cells would be collected, e.g., by centrifugation, and lysed using denaturants commonly known in the art.

The PTH variants may be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins. See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference. For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Protease inhibitors are particularly desired when cells must be lysed in order to isolate and purify the expressed polypeptide or protein.

A PTH variant or specified portion can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, mixed mode chromatography (e.g., MEP Hypercel™), hydroxyapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y. (1997-2003).

Neutralization after protein A purification should be done carefully to avoid aggregation/precipitation of the PTH-Fc fusion protein.

PTH variants or specified portions of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure and the specific PTH variant, the PTH variant or specified portion of the present invention may be glycosylated or can be non-glycosylated.

Formulations

In some embodiments, the pharmaceutical compositions described herein further comprise a carrier. Suitable acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., diluents, buffers, lipophilic solvents, preservatives, adjuvants, lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In some embodiments, a water-soluble carrier suitable for intravenous administration is used.

Pharmaceutically acceptable auxiliaries are preferred. Non-limiting examples of, and methods of preparing such sterile solutions are well known in the art, such as, but limited to, Gennaro, Ed., Remington's Pharmaceutical Sciences, $18^{th}$ Edition, Mack Publishing Co. (Easton, Pa.) 1990. Pharmaceutically acceptable carriers can be routinely selected that are suitable for the mode of administration, solubility and/or stability of the PTH variant composition as well known in the art or as described herein. For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. Preferred buffer ranges are pH 4-8, or pH 6.5-8, or pH 7-7.5. Preservatives, such as para, meta, and ortho-cresol, methyl- and propylparaben, phenol, benzyl alcohol, sodium benzoate, benzoic acid, benzyl-benzoate, sorbic acid, propanoic acid, esters of p-hydroxybenzoic acid may be provided in the pharmaceutical composition. Stabilizers, preventing oxidation, deamidation, isomerisation, racemisation, cyclisation, peptide hydrolysis, such as, e.g., ascorbic acid, methionine, tryptophane, EDTA, asparagine, lysine, arginine, glutamine and glycine may be provided in the pharmaceutical composition. Stabilizers, preventing aggregation, fibrillation, and precipitation, such as sodium dodecyl sulfate, polyethylene glycol, carboxymethyl cellulose, cyclodextrine may be provided in the pharmaceutical composition. Organic modifiers for solubilization or preventing aggregation, such as ethanol, acetic acid or acetate and salts thereof may be provided in the pharmaceutical composition. Isotonicity makers, such as salts, e.g., sodium chloride or carbohydrates, e.g., dextrose, mannitol, lactose, trehalose, sucrose or mixtures thereof may be provided in the pharmaceutical composition.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/PTH variant components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients may be used, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like.

PTH variant compositions can also include a buffer or a pH adjusting agent; typically, the buffer is a salt prepared from an organic acid or base. Exemplary buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

Additionally, the PTH variant compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the PTH variant compositions according to the invention are known in the art, e.g., as listed in "Remington: The Science & Practice of Pharmacy", 21$^{st}$ ed., Williams & Williams, (2005), and in the "Physician's Desk Reference", 71$^{st}$ ed., Medical Economics, Montvale, N.J. (2017), the disclosures of which are entirely incorporated herein by reference. Preferred carrier or excipient materials are salts (e.g., sodium chloride), carbohydrates (e.g., mannitol) and buffers (e.g., citrate).

The pharmaceutical compositions may be formulated as a liquid suitable for administration by intravenous or subcutaneous injection or infusion. The liquid may comprise one or more solvents. Exemplary solvents include but are not limited to water; alcohols such as ethanol and isopropyl alcohol; vegetable oil; polyethylene glycol; propylene glycol; and glycerin or mixing and combination thereof. A water-soluble carrier suitable for intravenous administration may be used. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

As noted above, formulations can preferably include a suitable buffer with saline or a chosen salt, as well as optional preserved solutions and formulations containing a preservative as well as multi-use preserved formulations suitable for pharmaceutical or veterinary use, comprising at least one PTH variant in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

The PTH variants may be formulated for parenteral administration and can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446.

The pharmaceutical compositions may be an extended release formulation. The pharmaceutical compositions may also be formulated for sustained release, extended release, delayed release or slow release of the PTH variant, e.g., comprising the amino acid sequence of SEQ ID NO: 8. Extended release, also known as controlled release and sustained release, can be provided to injectable formulations. Microspheres, nanospheres, implants, depots, and polymers may be used in combination with any of the compounds, methods, and formulations described herein to provide an extended release profile.

The PTH variants of the invention, e.g., comprising the amino acid sequence of SEQ ID NO: 8, may be formulated in a concentration of about 0.001 to about 100 mg/mL, or about 0.005 to about 50 mg/mL, or about 0.007 to about 20 mg/mL, or about 0.01 to about 10 mg/mL, or about 0.05 to about 5.0 mg/mL, or about 0.07 to about 2.0 mg/mL, or about 0.1 to about 1.0 mg/mL. In one embodiment, the PTH variant may be formulated in a concentration of about 0.01 to about 10 mg/mL. In one embodiment, the PTH variant may be formulated in a concentration of about 0.1 to about 1.0 mg/mL.

Formulations and compositions comprising the PTH variant can optionally further comprise an effective amount of at least one compound or protein selected from at least one of a diabetes or insulin metabolism related drug, an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immuno-modulation drug, an ophthalmic, otic or nasal drug, a topical drug, a nutritional drug or the like. Such drugs are well known in the art, including formulations, indications, dosing and administration for each presented herein (see e.g., Nursing 2001 Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmacotherapy Handbook, Wells et al., ed., Appleton & Lange, Stamford, Conn., each entirely incorporated herein by reference).

PTH variants may also be formulated as a slow release implantation device for extended or sustained administration of the PTH variant. Such sustained release formulations may be in the form of a patch positioned externally on the body. Examples of sustained release formulations include composites of biocompatible polymers, such as poly(lactic acid), poly(lactic-co-glycolic acid), methylcellulose, hyaluronic acid, sialic acid, silicate, collagen, liposomes and the like. Sustained release formulations may be of particular interest when it is desirable to provide a high local concentration of a PTH variant peptibody.

PTH variant compositions and formulations can be provided to patients as clear solutions or as dual vials comprising a vial of lyophilized at least one PTH variant (e.g., comprising the amino acid sequence of SEQ ID NO: 8) or specified portion or variant that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

PTH variant compositions and formulations can be provided indirectly to patients by providing to pharmacies, clinics, or other such institutions and facilities, clear solutions or dual vials comprising a vial of lyophilized at least one PTH variant (e.g., comprising the amino acid sequence of SEQ ID NO: 8) or specified portion or variant that is reconstituted with a second vial containing the aqueous diluent. The clear solution in this case can be up to one liter or even larger in size, providing a large reservoir from which smaller portions of a PTH variant (e.g., comprising the amino acid sequence of SEQ ID NO: 8) or specified portion or variant solution can be retrieved one or multiple times for transfer into smaller vials and provided by the pharmacy or clinic to their customers and/or patients. Such products can include packaging material. The packaging material can provide, in addition to the information required by the regulatory agencies, the conditions under which the product can be used. The packaging material can provide instructions to the patient to reconstitute a PTH variant (e.g., comprising the amino acid sequence of SEQ ID NO: 8) or specified portion or variant in the aqueous diluent to form a solution and to use the solution over a period of 2-24 hours or greater for the two vial, wet/dry product.

Treatment

In another aspect is provided a method for treating a subject with hypoparathyroidism and/or hypocalcemia due to hypoparathyroidism comprising treating the subject with a PTH variant of the invention using a dosing regimen effective to control serum and urinary calcium levels of the subject. The PTH variants may be particularly effective to treat hypoparathyroidism and/or hypocalcemia due to hypoparathyroidism because they have a longer half-life than native PTH(1-84). A greater half-life allows for daily administration and maintenance of PTH variants at more physiologically relevant levels which allows for a more sustained control over both serum and urinary calcium.

In some embodiments, the method is effective to control serum calcium levels of a subject. In one embodiment, the method is effective to increase serum calcium levels of a subject with hypoparathyroidism and/or hypocalcemia due to hypoparathyroidism as compared to the serum calcium levels of said subject in the absence of administration of the PTH variant of the invention. In one embodiment, the method is effective to maintain serum calcium levels of a subject at a lower peak-to-trough ratio as compared to the serum calcium levels of a subject receiving exogenous native PTH(1-84). In one embodiment, the method is effective to reduce the amount of calcium supplements of a subject with hypoparathyroidism.

In some embodiments, the method is effective to control urinary calcium secretion of a subject. In one embodiment, the method is effective to decrease urinary calcium output to the levels of healthy volunteers (reduce potential kidney complications).

The PTH variant, e.g., comprising the amino acid sequence of SEQ ID NO: 8, may be administered subcutaneously or intravenously. In various embodiments, multiple administrations are performed according to a dosing regimen. As used herein, the term "QD" or "q.d." means administration once a day, "Q2D" means administration every two days, etc. "QW" means administration every week. "BID" means administration twice a day. Dosing can be undertaken BID, once per day (QD), Q2D, Q3D, Q4D, QSD, Q6D, QW, once every 8 days, once every 9 days, once every 10 days, once every 11 days, once every 12 days, once every 13 days, once every two weeks, once every 15 days, once every 16 days, or once every 17 days, once every three weeks, or once every month, for example.

The PTH variant (e.g., comprising the amino acid sequence of SEQ ID NO: 8) may be administered subcutaneously according to a dosage regimen of between 0.001 μg to 1,000 μg, twice a day, or once per day, or every two days, or every 5-8 days, or every week (QW). Alternatively, the PTH variant could be administered every three weeks or once a month, such as for maintenance purposes.

PTH variant (e.g., comprising the amino acid sequence of SEQ ID NO: 8) may be administered subcutaneously according to a dosage regimen of from about 1 μg per day to about 500 μg per day, or about 2 μg per day to about 250 μg per day, or about 5 μg per day to about 100 μg per day, or about 10 μg per day to about 80 μg per day, or about 20 μg per day to about 100 μg per day, or about 20 μg per day to about 100 μg per day, or about 50 μg, or about 60 μg, or about 70 μg, or about 80 μg, or about 90 μg, or about 100 μg once per day (QD). The PTH variant (e.g., comprising the amino acid sequence of SEQ ID NO: 8) may be administered in a concentration of 0.001 to 1,000 μg/mL.

The above dosing regimens may be conducted for a period of one month, or two months, or six months, or one year, or two years, or five years, or longer than five years to treat hypoparathyroidism and/or hypocalcemia due to hypoparathyroidism. PTH variants can be administered for the duration of a subject's lifetime for maintenance.

As used herein, the term "subcutaneous tissue", is defined as a layer of loose, irregular connective tissue immediately beneath the skin. For example, the subcutaneous administration may be performed by injecting a composition into areas including, but not limited to, the thigh region, abdominal region, gluteal region, or scapular region. For such purposes, the formulation may be injected using a syringe. However, other devices for administration of the formulation are available such as injection devices (e.g., the Injectease™ and Genject™ devices); injector pens (such as the Q-Cliq™ and GenPen™); needleless devices (e.g., MediJector™ and BioJector™); and subcutaneous patch delivery systems. In some embodiments, a PTH variant, e.g., comprising the amino acid sequence of SEQ ID NO: 8, or a pharmaceutical composition containing the same is administered intravenously.

In various embodiments, the above methods of treating hypoparathyroidism and/or hypocalcemia due to hypoparathyroidism are used in conjunction with other methods treat hypoparathyroidism and/or hypocalcemia due to hypoparathyroidism.

EXAMPLES

The following examples illustrate specific aspects of the instant description. The examples should not be construed as limiting, as the examples merely provide specific understanding and practice of the embodiments and their various aspects.

Example 1: Fc Fusion PTH Variant (Exemplified by PTH-66) Production and Purification PTH-66 was transiently expressed in CHO cells, and conditioned media was stored at −20° C. until further use. Conditioned media was defrosted at a 25° C. water bath and filtered through a 0.2 µm bottle top filter unit. PTH-66 protein was purified on protein A-derived resin MabSelect SuRe following the manufacture's protocol (FIG. 8). MabSelect SuRe column was pre-equilibrated with PBS. Defrosted conditioned media was loaded on column followed by extensive wash with PBS. PTH-66 protein was eluted by step elution with 100 mM Sodium Citrate Buffer pH 3.2. Elution fractions were analyzed on SDS-PAGE (FIG. 9). The pH of pooled elution fractions was brought up to about pH 6 with 1 M Tris pH 10. Neutralized pooled elution fractions were dialyzed into PTH-66 Storage Buffer 20 mM sodium phosphate buffer, 50 mM sodium chloride, 26 mg/ml mannitol, pH 6.0 and stored at −80° C.

Figure 8A:
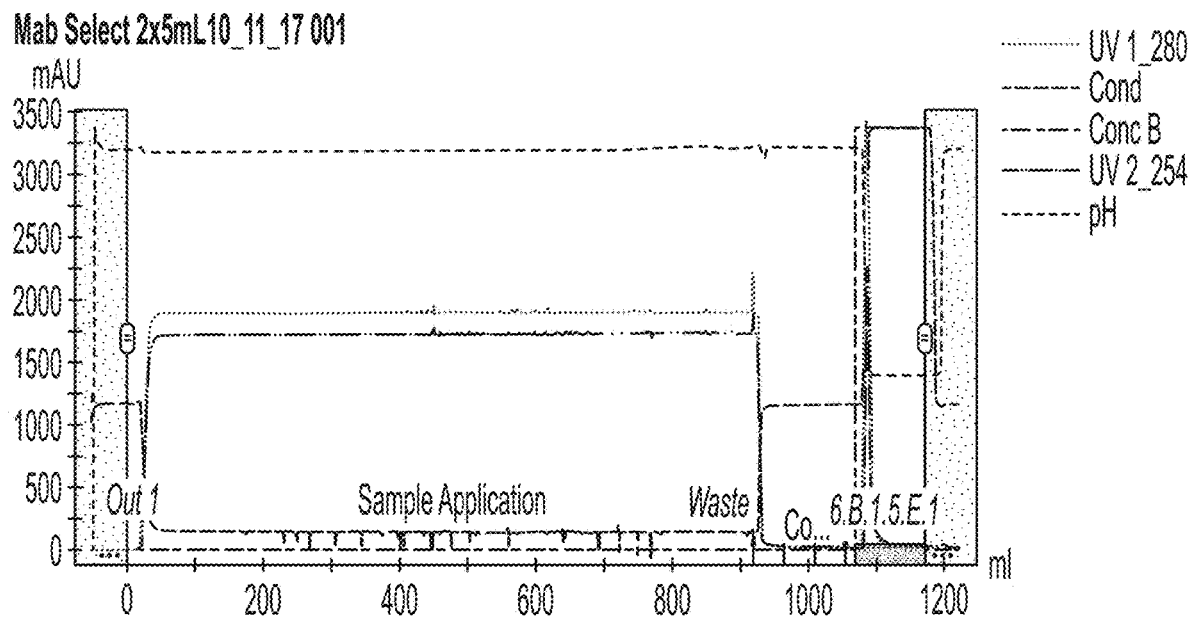
FIG. 8A depicts a trace of chromatographic purification of ~900 mL CM expressing PTH-66 using 2×5 mL Mab Select Sure columns. 8B is a flowchart outlining the purification steps of PTH-66 according to an embodiment of the invention.
Figure 8B:
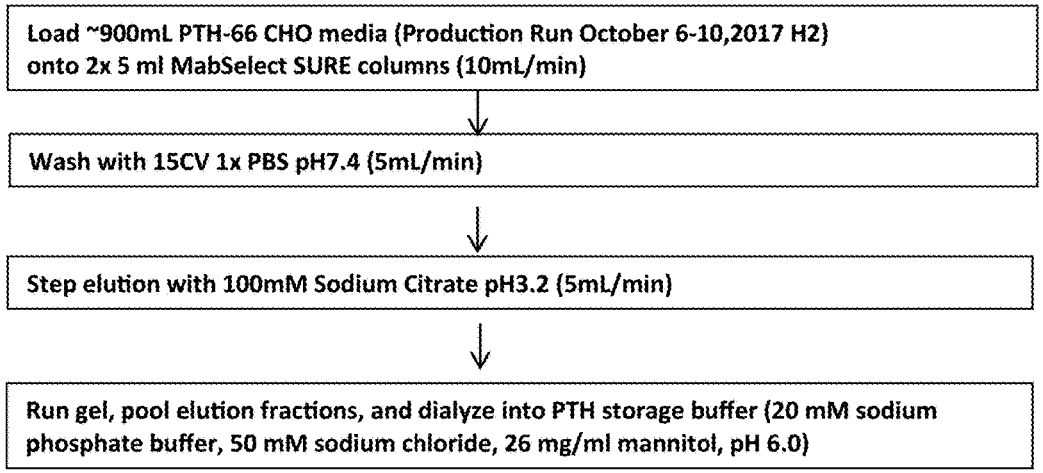

FIG. 8A depicts a trace of chromatographic purification of ~900 mL CM expressing PTH-66 using 2×5 mL Mab Select Sure columns. FIG. 8B is a flowchart outlining the purification steps of PTH-66 according to an embodiment of the invention.

Figure 9A:
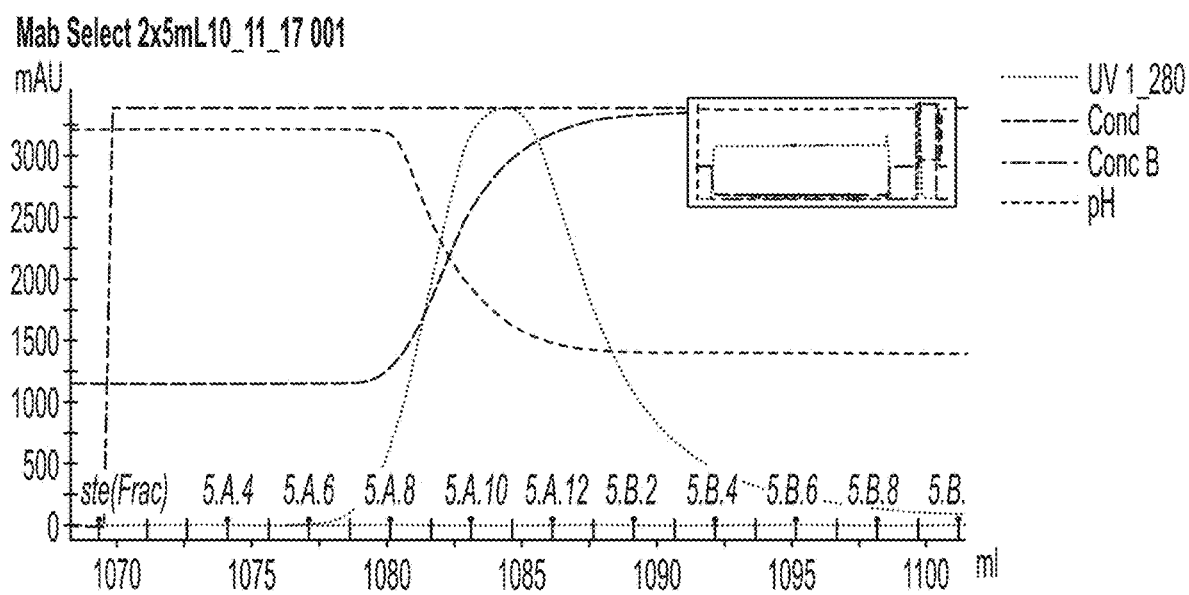
FIG. 9A depicts Mab select crude elution fractions of PTH-66.
Figure 9B:
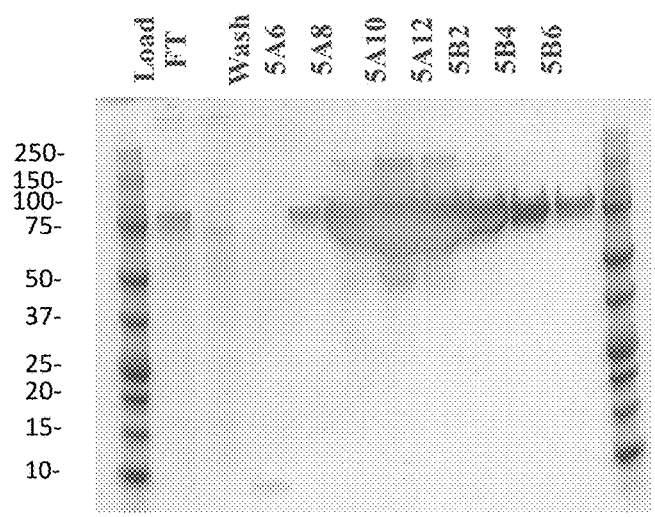
FIG. 9B depicts Coomassie blue staining for Mab select crude elution fractions of PTH-66.

FIG. 9A depicts Mab select crude elution fractions of PTH-66. FIG. 9B depicts Coomassie blue staining for Mab select crude elution fractions of PTH-66.

Figure 10:
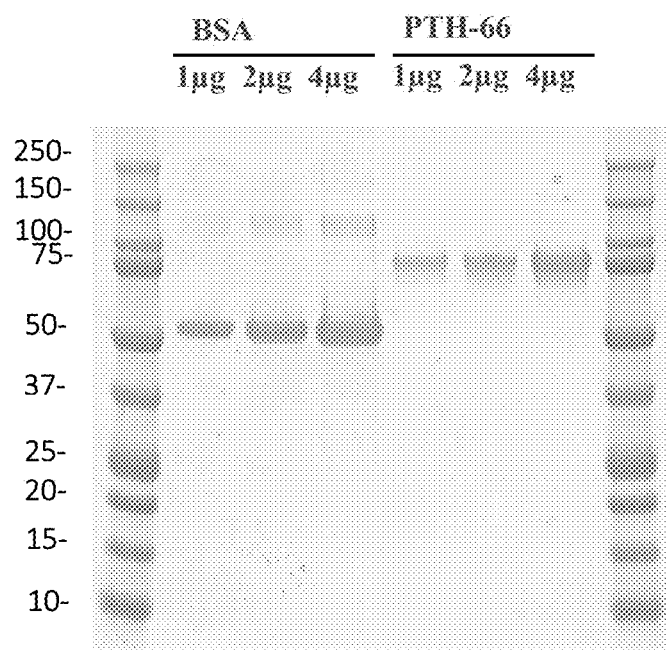
FIG. 10 depicts an SDS-PAGE Coomassie stain of the final PTH-66 product.

FIG. 10 depicts the SDS-PAGE Coomassie stain of final PTH-66 product. Final yield was about 75 mg per 900 mL cell medium (CM). Protein is at 3 mg/mL in PTH storage buffer. Protein was aliquoted and stored at −80° C.

Example 2: Effect of C-Terminal Truncation of PTH-Fc Fusions

PTH-Fc fusion variants comprising truncated PTH of varying lengths were prepared according to the methodology outlined in Example 1. The following PTH-Fc fusion variants were created: PTH-66 (PTH(1-74)-Fc), PTH-67 (PTH(1-64)-Fc), PTH-68 (PTH(1-54)-Fc), PTH-69 (PTH(1-44)-Fc), and PTH(1-34)-Fc.

Serum concentrations of PTH following single subcutaneous treatment of Sprague-Dawley rats at 0.25 mg/kg with the truncated variants and full-length PTH(1-84)-Fc were assessed using Immunotopics bioactive ELISA kit (60-3000), and the results are shown in FIG. 1.

As shown in FIG. 1, C-terminal truncation of PTH surprisingly and unexpectedly improves exposure and pharmacokinetics of PTH-Fc fusions.

As the figure demonstrates, truncated PTH-Fc fusion variants of the invention outperform both the native-length PTH(1-84)-Fc fusion and teriparatide-Fc (PTH(1-34)-Fc fusion). Even more surprisingly, PTH(1-74) has a particularly long half-life in vivo, as compared to the native-length PTH(1-84)-Fc and other analogs.

Example 3: PTH-66 in Normal Mice

PTH-66 was administered to normal mice at the dose of 50 nmol/kg. Samples were taken at 2, 8, 24, 48, and 72 hours after administration, and calcium concentrations were plotted and compared to the phosphate buffer (vehicle) control.

Figure 2A:
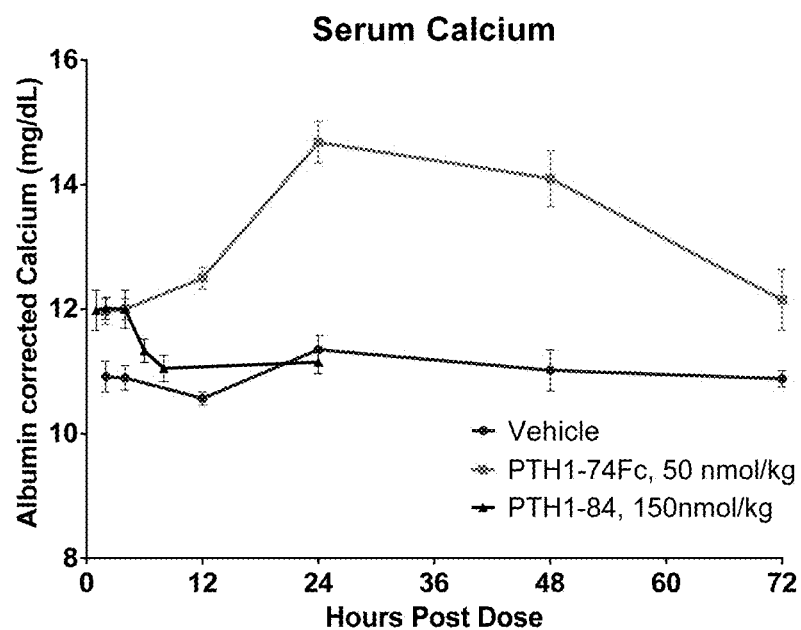
FIGS. 2(A-B) show serum calcium (FIG. 2A) and urine calcium (FIG. 2B) concentrations as a function of time for PTH-66 (PTH(1-74)-Fc fusion) as compared to the vehicle (phosphate buffer) control, following single subcutaneous administration in mice.
Figure 2B:
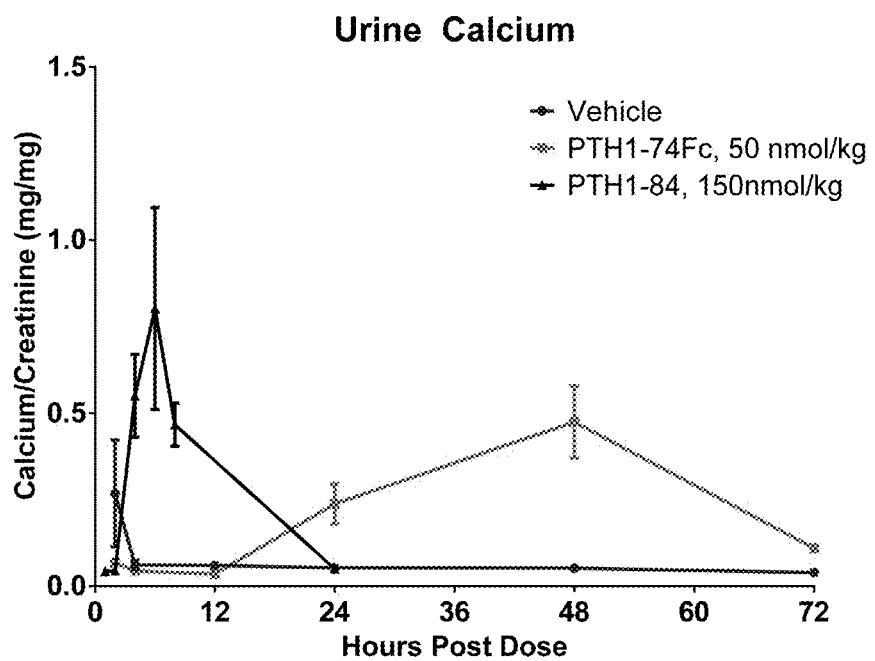

FIG. 2 illustrates serum calcium levels (FIG. 2A) and urine calcium levels (FIG. 2B) as a function of hours post dose for PTH-66 (50 nmol/kg dose) in mice. As shown in FIG. 2A, PTH-66 elicits a long-lasting increase in serum calcium, as compared to PTH(1-84) and a vehicle control. FIG. 2B, PTH-66 shows longer maintenance of urine calcium level than PTH(1-84). PTH(1-84) treatment results in a spike in urine calcium within the first few hours, consistent with the rise in serum calcium and transient exposure of the molecule. In contrast, despite the elevated serum calcium level, PTH-66 demonstrates a longer lasting control of urine calcium level, maintaining levels close to vehicle for 12-24 hours. In summary, treatment with PTH-66 leads to a sustained effect on calcium levels.

Example 4: PTH-66 in TxPTx Rats

PTH-66 was administered to normal (intact) and thyroparathyroidectomized (TxPTx) rats at varying doses of 5, 20, and 60 nmol/kg. Serial samples were taken at 1, 6, 12, 18, 24, 36, 48, and 72 hours after administration, and compared to a vehicle control.

Figure 3A:
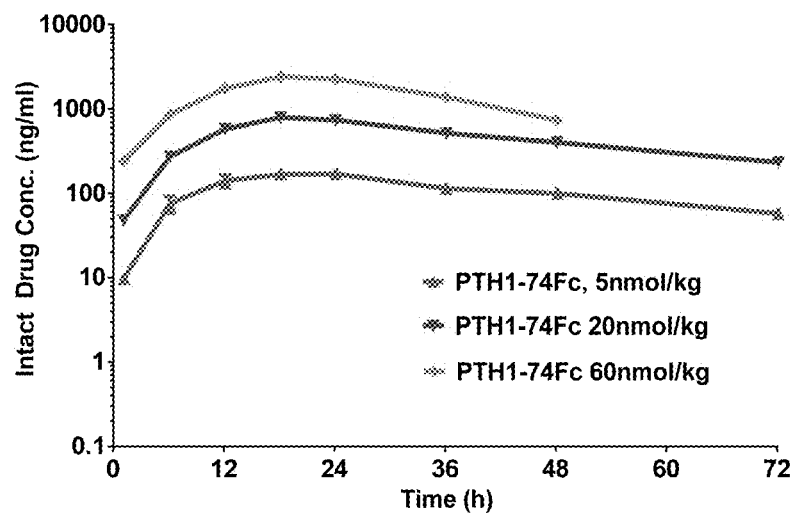
FIGS. 3(A-B) show the PK (FIG. 3A) and PD (FIG. 3B) data for PTH-66 (PTH(1-74)-Fc) fusion on serum calcium in TxPTx rats at various concentrations following a single subcutaneous injection.
Figure 3B:
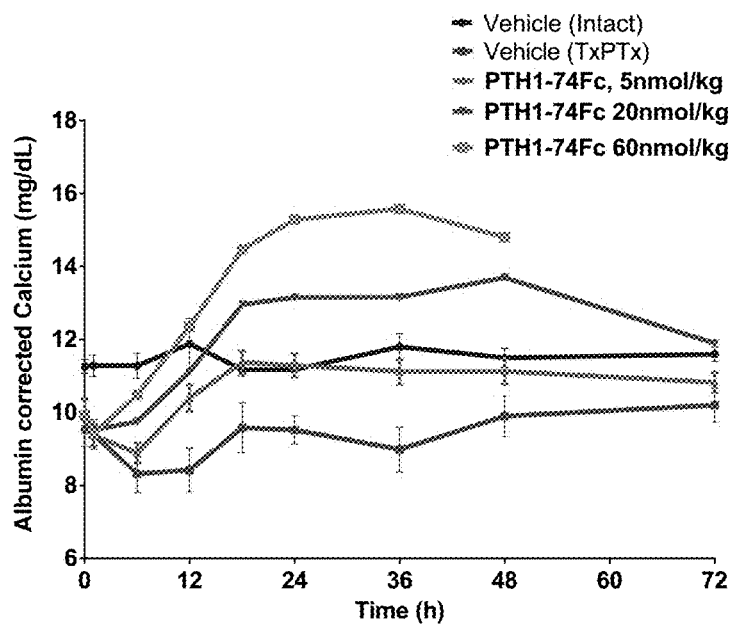

As shown in FIGS. 3A and B, TxPTx rats treated with PTH-66 show a dose linear PK/PD response with dose-dependent serum Ca++ levels that are elevated and maintained for up to 72 hours after administration. FIG. 3B shows that TxPTx rats receiving 5 nmol/kg PTH-66 have normalized serum calcium levels that return to that of the intact rats while treatment with 20 and 60 nmol/kg PTH-66 show higher serum calcium levels as compared to intact rats receiving a placebo vehicle at 12-48 hours after administration.

Figure 4A:
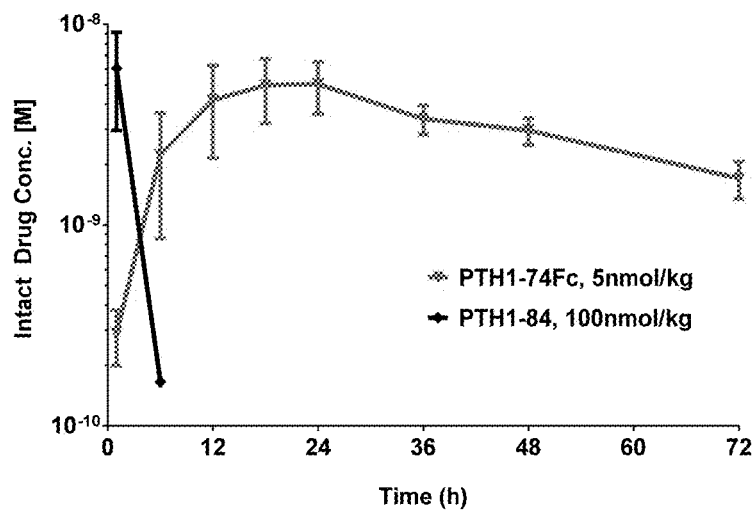
FIGS. 4(A-B) show single dose PK (FIG. 4A) and PD (FIG. 4B) study data from TPTx rats comparing PTH-66 to PTH(1-84).
Figure 4B:
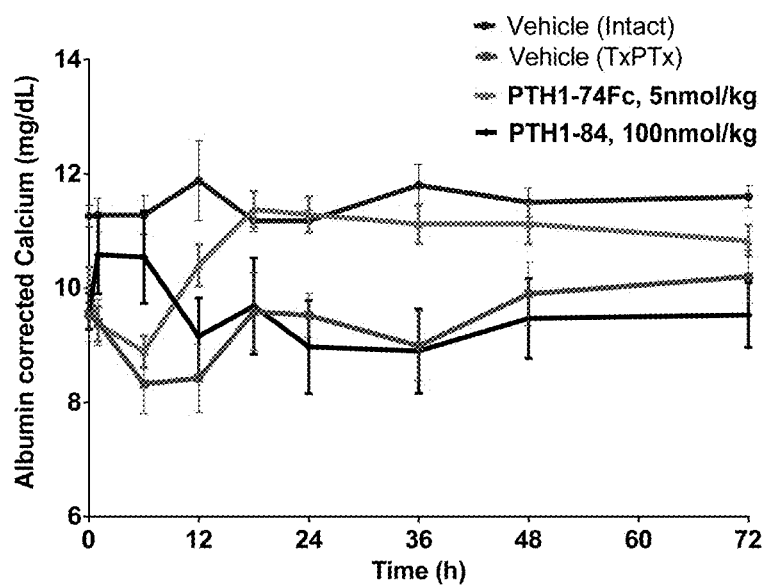
Figure 5A:
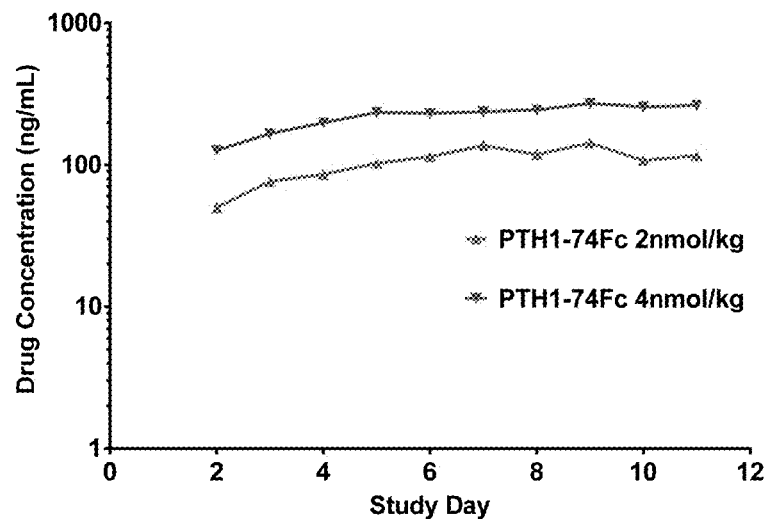
FIGS. 5(A-D) show multi-dose PK (FIG. 5A) and PD (FIG. 5B-D) study data from daily subcutaneous administration of PTH-66 to TPTx rats.
Figure 5B:
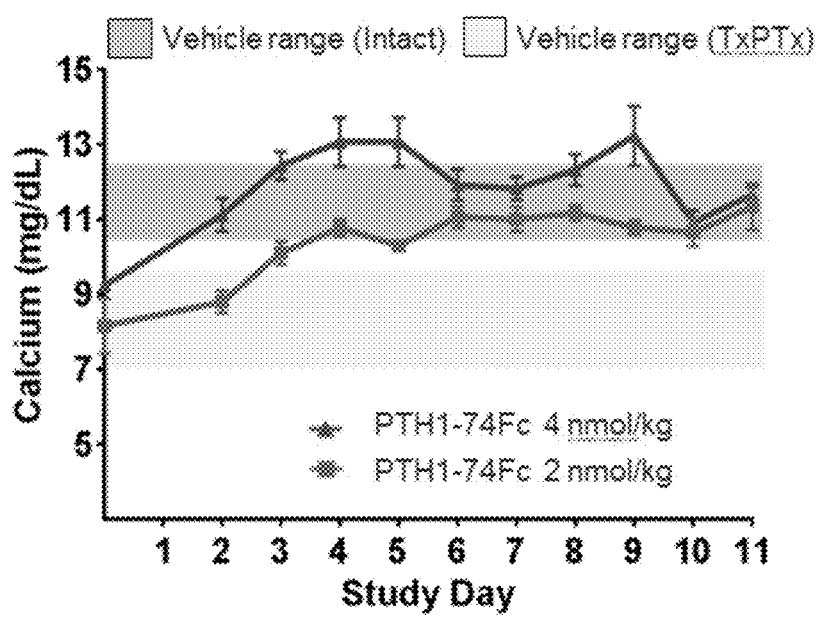
Figure 5C:
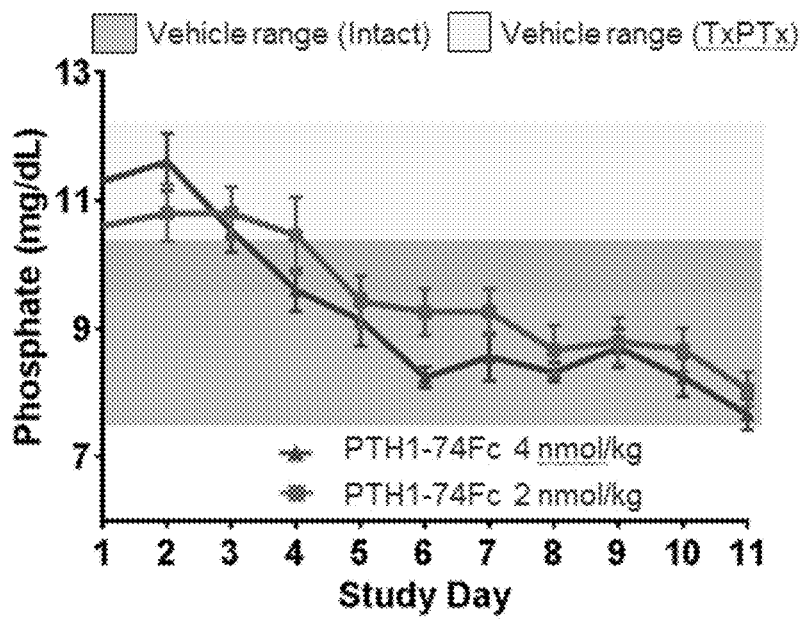
Figure 5D:
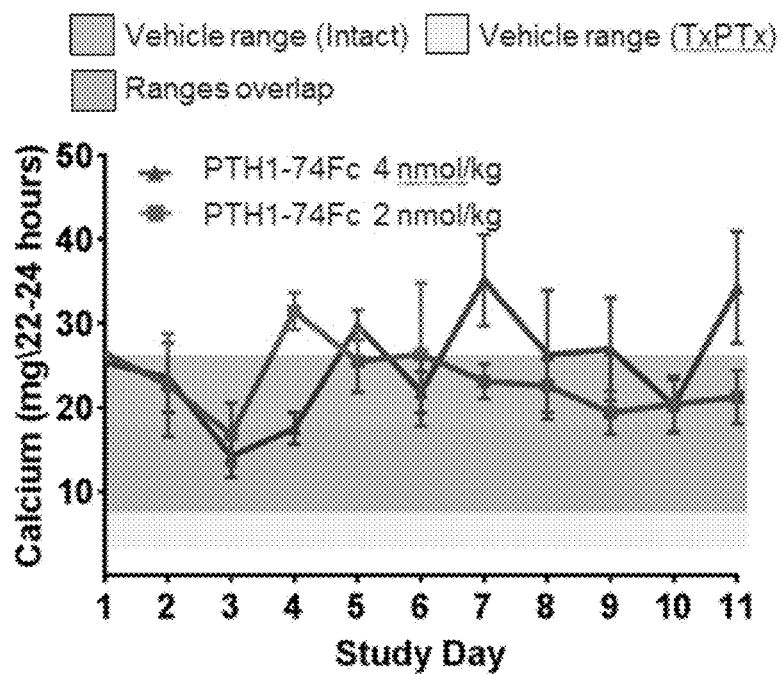

FIGS. 4(A-B) show single dose PK (FIG. 4A) and PD (FIG. 4B) study data from TPTx rats comparing PTH-66 to PTH(1-84). Rat TPTx Data shows obvious PK extension beyond PTH(1-84) and that PTH-66 at 5 nmol/kg can return serum calcium to normal levels as compared to PTH(1-84) which shows only a very transient increase in serum calcium.

In a separate multidose study, PTH-66 was administered daily subcutaneously to normal (intact) and thyro-parathyroidectomized (TxPTx) rats at the doses of 2 and 4 nmol/kg for 10 days. Samples were taken once daily prior to dosing and compared to a vehicle control.

FIGS. 5(A-D) show multi-dose PK (FIG. 5A) and PD (FIG. 5B-D) study data from daily subcutaneous administration of PTH-66 to TPTx rats. FIG. 5A PK data shows a dose linear PK response with close to steady state levels of PTH-66 achieved. As FIG. 5B shows, 2 and 4 nmol/kg PTH-66 returns and maintains serum calcium to the normal range (intact) levels. FIG. 5C shows that daily administration of PTH-66 also results in normalization of serum phosphate levels. FIG. 5D shows that while PTH-66 is maintaining normal serum calcium levels as shown in FIG. 5A, the molecule is also maintaining normal urine calcium level. These data show that daily subcutaneous administration of PTH-66 results in full normalization of serum calcium and phosphate and importantly, urine calcium.

Example 5: PTH-66 in Primates

Figure 6A:
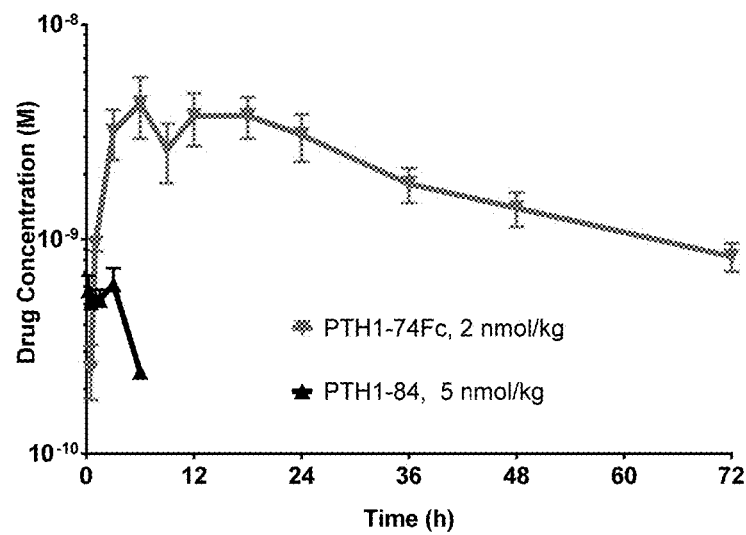
FIGS. 6(A-B) show single-dose PK (FIG. 6A) and PD (FIG. 6B) study data from wild type cynomolgus monkey comparing PTH-66 to PTH(1-84).
Figure 6B:
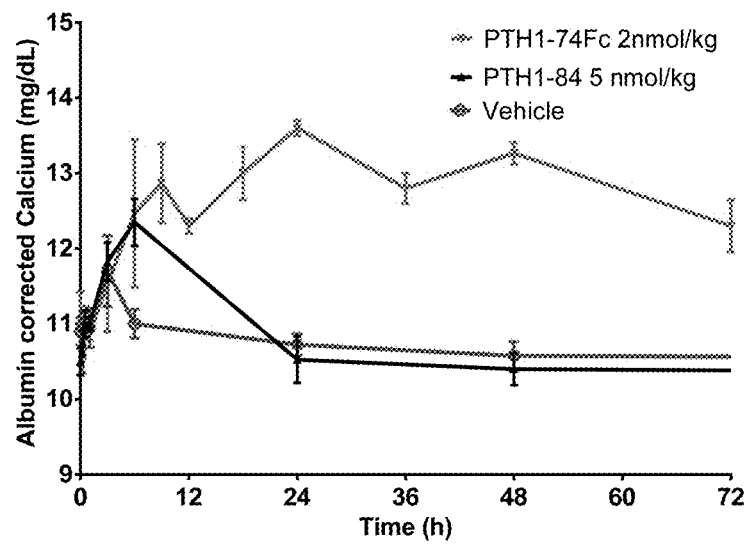

PTH-66 was administered to wild type Cynomolgus monkeys as a single dose at the dosage of 2 mmol/kg, while other monkeys received a single dose of 5 mmol/kg of Natpara (PTH(1-84)). Serial samples were taken at 0, 1, 3, 6, 9 12, 18 24, 36, 48, and 72 hours after administrations, and compared to Natpara as well as a vehicle control FIGS. 6(A-B) show single-dose PK (FIG. 6A) and PD (FIG. 6B) study data from Wild type Cynomolgus monkey comparing PTH-66 to PTH(1-84).

The data in FIG. 6 shows obvious PK extension in PTH-66 beyond Natpara, and that PTH-66 at 2 nmol/kg can stimulate and maintain serum calcium levels beyond that obtained with PTH(1-84). Compared to PTH-66, Natpara is short-lived and has more transient impact on serum calcium.

In a separate multidose study, PTH-66 was administered daily, subcutaneously, for 9 days to wild type Cynomolgus monkeys at a dosage of 1 nmol/kg. Samples were taken daily prior to dosing and 24, 48, 72, and 120 hr following the last dose and compared to vehicle control.

Figure 7:
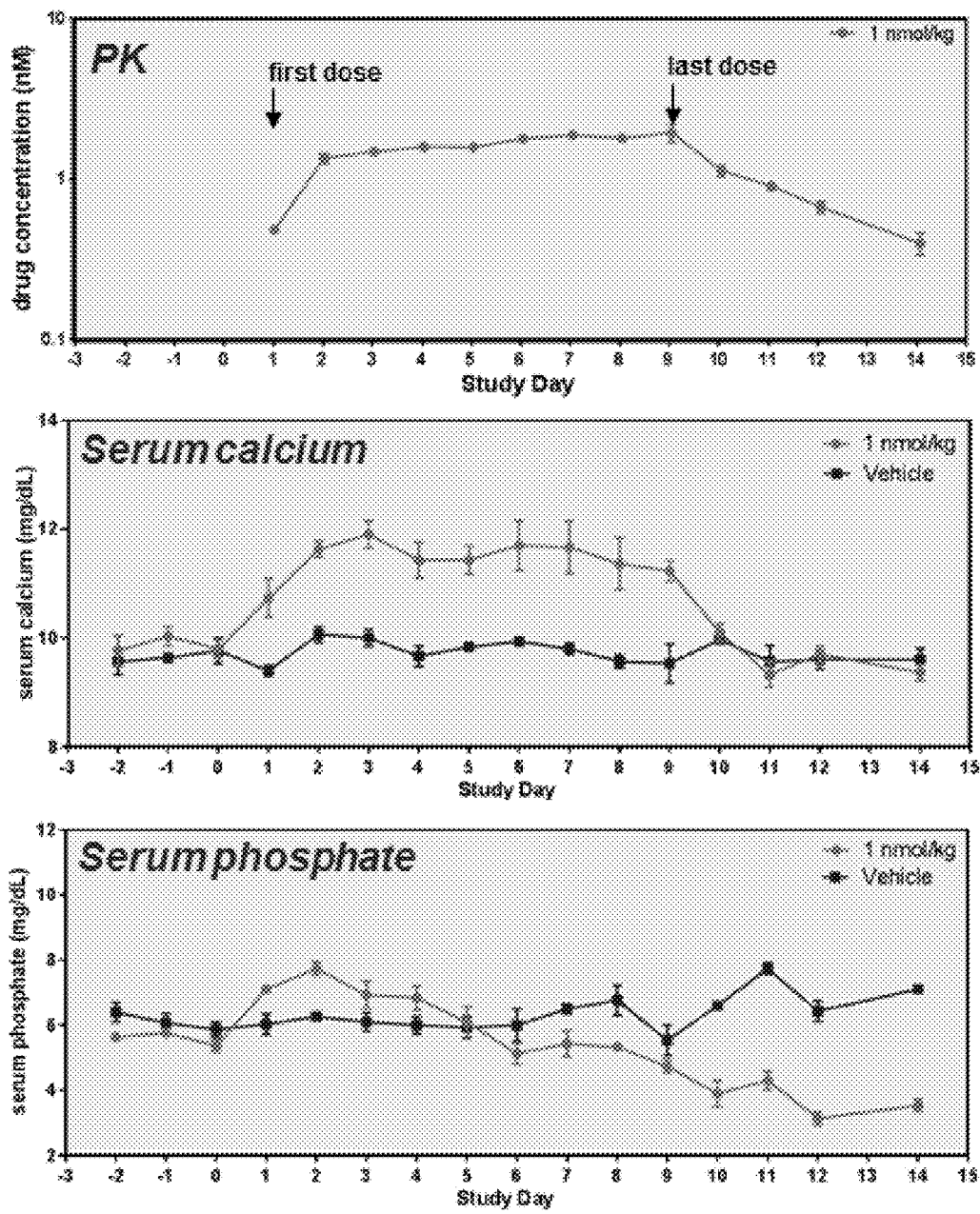
FIG. 7 shows multidose PK and PD study data from wild type cynomolgus monkey comparing PTH-66 to vehicle following daily subcutaneous administration.

FIG. 7 shows multidose PK and PD study data from daily subcutaneous treatment of wildtype cynomolgus monkeys with 1 nmol/kg PTH-66. The PK data indicate that a relatively flat PK profile of PTH-66 was achieved with a resultant increase in serum calcium and decrease in serum phosphate over the study period, relative to the vehicle control.

Example 6: PTH cAMP Potency Assay

Table 1 summarizes the results of the cAMP potency ($EC_{50}$) assay for exemplary PTH variants according to the invention. Table 2 summarizes pertinent PK data for PTH variants.

TABLE 1

$EC_{50}$ Data for Select PTH-Fc Variants

| Variant | Mutation | EC50 (nM) | $R^2$ |
| --- | --- | --- | --- |
| 1-34 | n/a | 0.22 | 0.97 |
| 1-84 | n/a | 0.24 | 0.98 |
| 1-84 Fc | F34A, V35S | 0.28 | 0.98 |
| 1-74 Fc | F34A, V35S | 0.24 | 0.98 |
| 1-64 Fc | F34A, V35S | 0.24 | 0.97 |
| 1-54 Fc | F34A, V35S | 0.21 | 0.97 |
| 1-34 Fc | n/a | 0.18 | 0.98 |

TABLE 2

PK Data for Select PTH-Fc Variants

| Variant | Mutation | Half-life (subcutaneous, hours) | IV Clearance (ml/hour/kg) | Bioavailability (%) |
| --- | --- | --- | --- | --- |
| 1-84 | N/A | 1 | 780 | 35 |
| 1-84 Fc | F34A, V35S | 3.8 | 50 | 0.7 |
| 1-74 Fc | F34A, V35S | 46 | 12 | 35.2 |
| 1-64 Fc | F34A, V35S | 37 | 17 | 35.9 |
| 1-54 Fc | F34A, V35S | 32 | 50 | 23.5 |

As shown in Tables 1 and 2, all PTH-Fc samples are active with sub-nanomolar $EC_{50}$s, and have significantly improved PK properties over that of PTH1-84.

Example 6: Multimodal Chromatography in PTH-66 Purification

Figure 11:
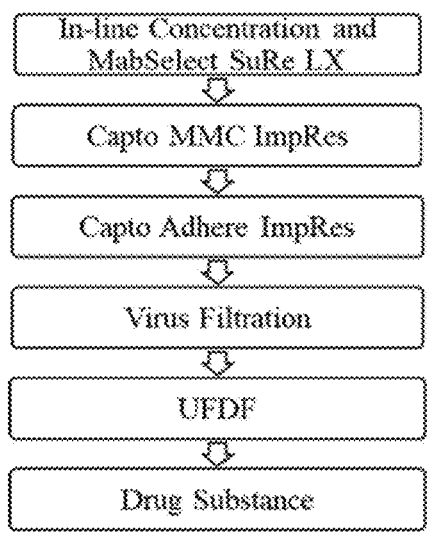
FIG. 11 depicts the PTH-66 downstream process flow.

Protein A chromatography as the initial capture step has been performed following the downstream platform depicted in FIG. 11. The elution is held at a low pH of 3.5 for one hour for virus inactivation followed by being neutralized to pH 6 and frozen at −80° C. The majority of impurities except for clipped species and host cell proteins have been sufficiently removed. Polishing steps described below have been developed to remove the residual host cell and process impurities.

The application of multimodal (also known as mixed mode) chromatography is growing rapidly in antibody purification in that the media allows compound separation at high efficiency through various interactions. Two multimodal column steps, cationic Capto™ MMC ImpRes and anionic Capto™ Adhere ImpRes, have been considered in the downstream polishing development. However, given the complicated media specific interactions, the purification process is determined by buffer component, ionic strength, pH, and salt type. As the optimal binding and elution conditions are difficult to estimate, the separation conditions of these two resins have been determined via the steps described below to achieve optimal process performance.

Figure 12:
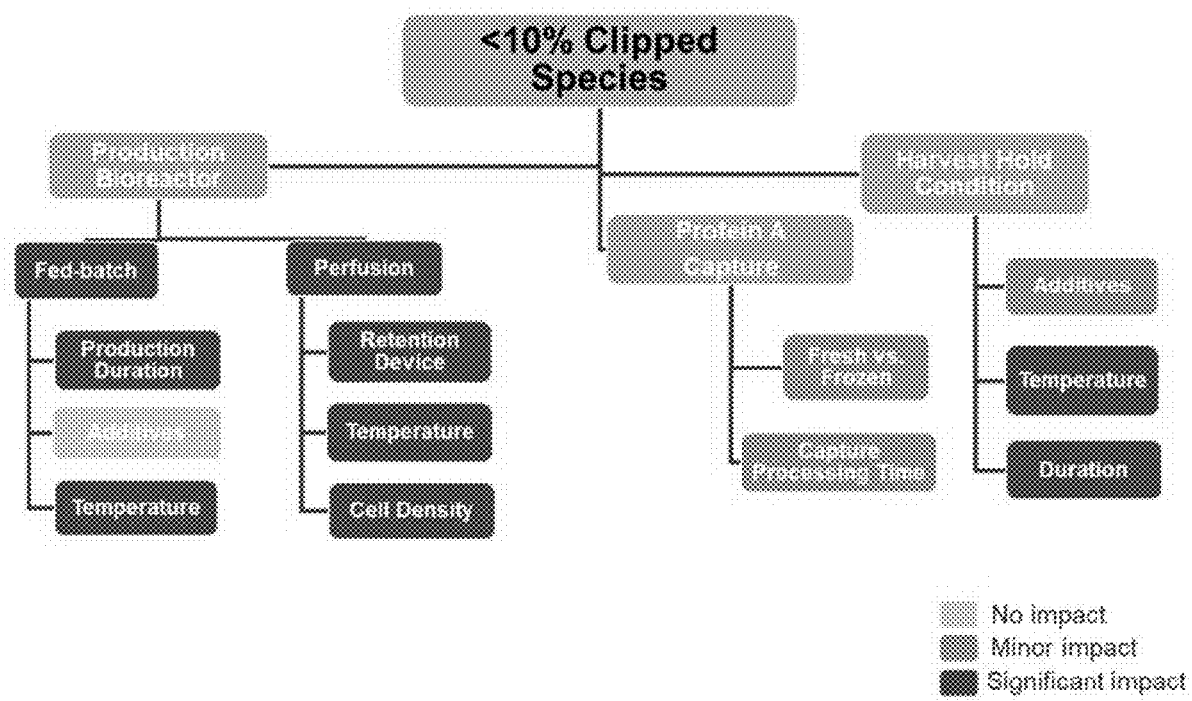
FIG. 12 is a flowchart of the production process for PTH-66 that meets the less than 10% fragmentation target.

PTH-66 (PTH(1-74)-Fc fusion) has seen moderate fragmentation from the bioreactor, which may negatively impact its potency despite the increased circulating half-life. Addition of protease inhibitor in harvested cell culture prior to downstream processing has been shown to protect against future product degradation. Fragmentation of recombinant protein in cell culture could be detrimental to drug safety and potency. In downstream process development, fragment isoforms with altered hydrophobicity or charge, generated from upstream process, have been successfully separated from the intact Fc-fusion protein using multimodal chromatography. The flowchart of the production process that meets the less than 10% fragmentation target is depicted in FIG. 12.

Thorough high-throughput screenings (HTS) for initial operation conditions of Capto MMC and Adhere ImpRes were performed using 6 μL PreDictor 96-well plates to evaluate a broad range of parameters including salt concentrations and pH (see FIGS. 13A and 13B).

Figure 14A:
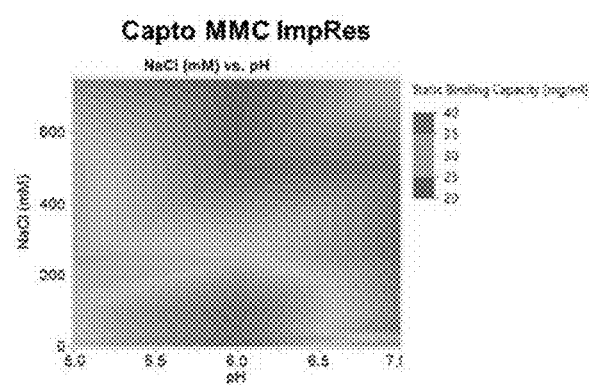
FIG. 14A is a plot of high-throughput screening of Capto MMC ImpRes.
Figure 14B:
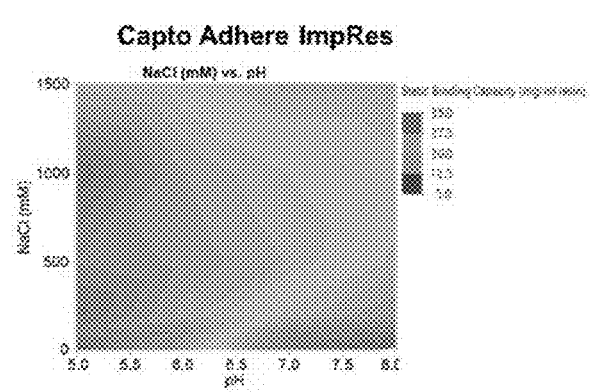
FIG. 14B is a plot of high-throughput screening of Capto Adhere ImpRes to determine optimal binding conditions.

The separation conditions of cation exchange (cationic) Capto MMC ImpRes and anion exchange (anionic) Capto Adhere ImpRes determined using the high-throughput process are depicted in FIGS. 14A and 14B. Screened experimental conditions for Capto MMC ImpRes included acetate, MES, and phosphate buffer systems, at pH 5.0 to 7.0 and salt (NaCl) concentrations from 0 to 750 mM at 50 g/L resin load and incubation time of 1 hour. Screened experimental conditions for Capto Adhere ImpRes included acetate, MES, phosphate and Tris buffer systems, at pH 5.0 to 8.0 and salt (NaCl) concentrations of 0 to 1500 mM at 50 g/L resin load and incubation time of 1 hour.

Figure 14C:
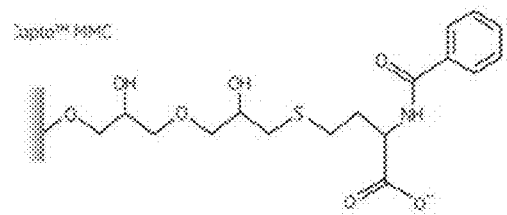
FIG. 14C is a chemical structure of Capto MMC.
Figure 14D:
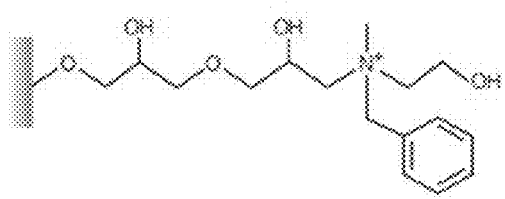
FIG. 14D is a chemical structure of Capto Adhere.

Optimal binding conditions for Capto MMC ImpRes, a cationic resin having the structure depicted in FIG. 14C, have been determined to include 50 mM MES at pH 6.0 without any salt. Optimal flow-through conditions for Capto Adhere ImpRes, an anionic resin having the structure depicted in FIG. 14D, have been determined to include 50 mM acetate buffer at pH 5.0 without any salt.

Figure 15:
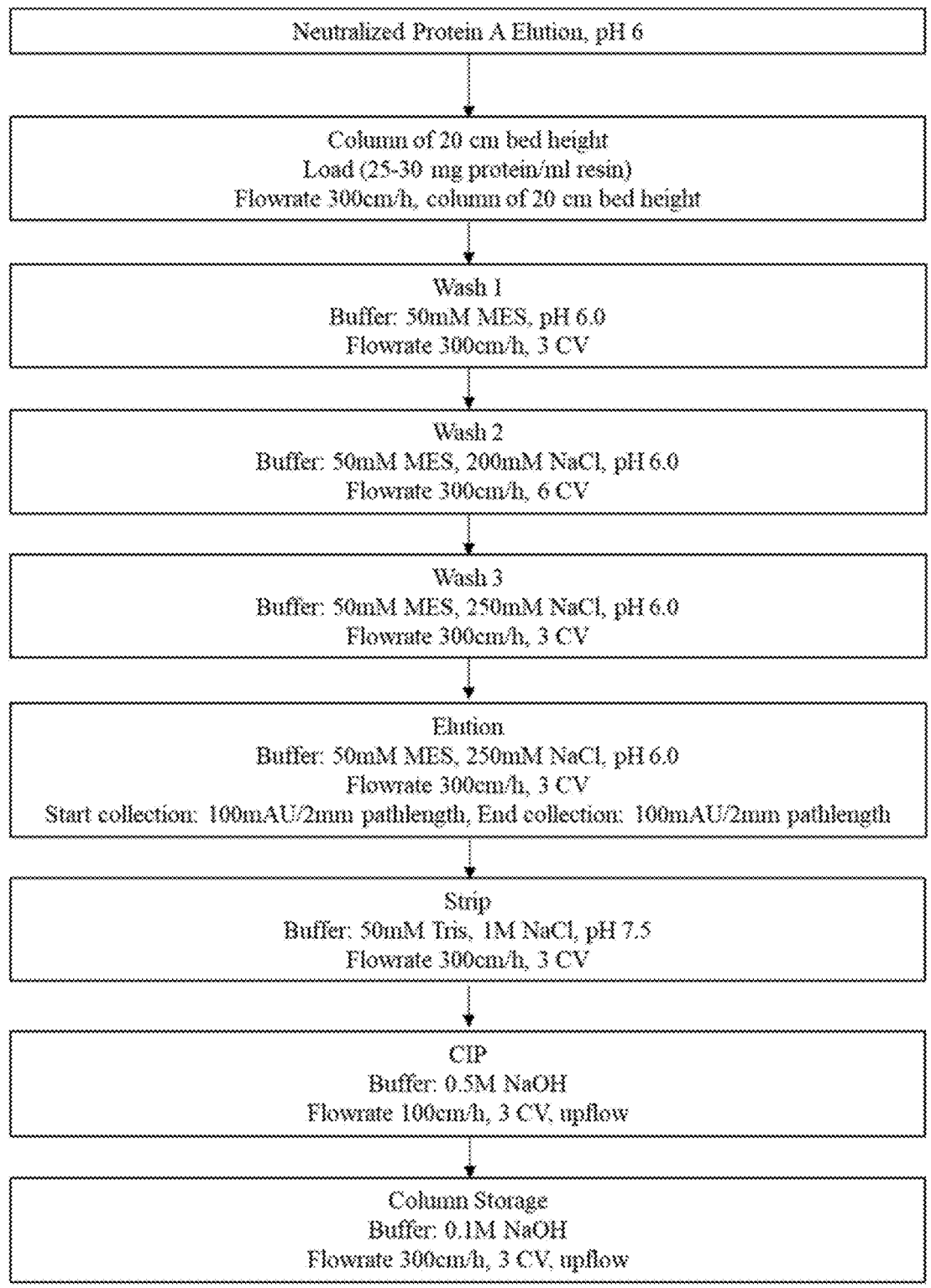
FIG. 15 depicts the Capto MMC ImpRes process flow.
Figure 16:
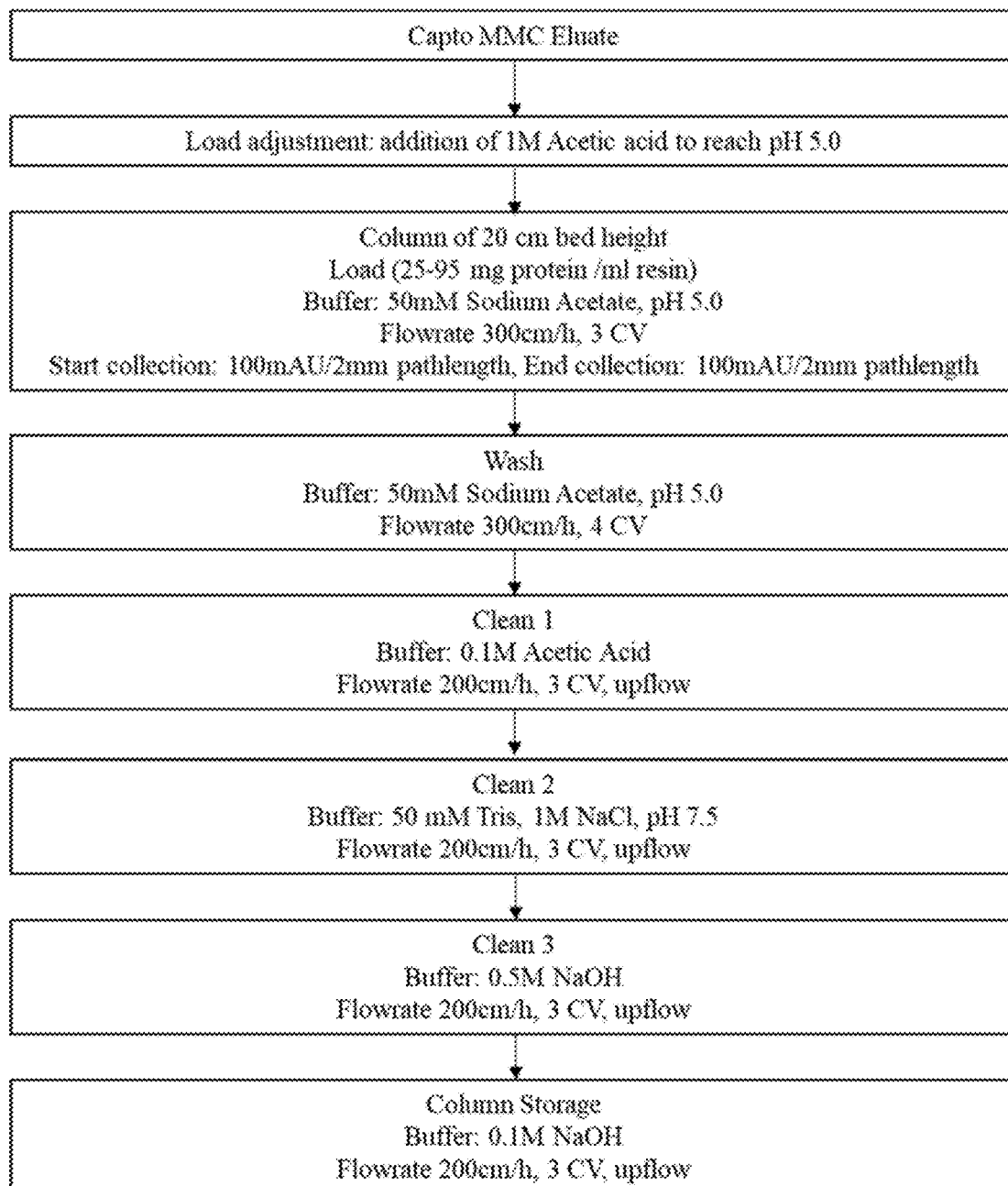
FIG. 16 depicts the Capto Adhere ImpRes process flow.

The second step is to optimize the process at bench-scale accelerated by the HTS static binding capacity results. Capto MMC ImpRes was conducted in bind-and-elute mode to maximize the impurity clearance capacity. The wash steps have been investigated to reduce excessive process- and product-related impurities without unnecessary product loss (FIG. 15). The subsequent Capto Adhere ImpRes step was developed as a fast flow-through (FT) step allowing the process to meet the product quality standards (FIG. 16). MMC and Adhere bench-top confirmation runs were conducted to validate the process robustness regarding impurity clearance and step yield. PTH-Fc quantification relies upon UV280 to track yields for MMC and Adhere.

Figure 17A:
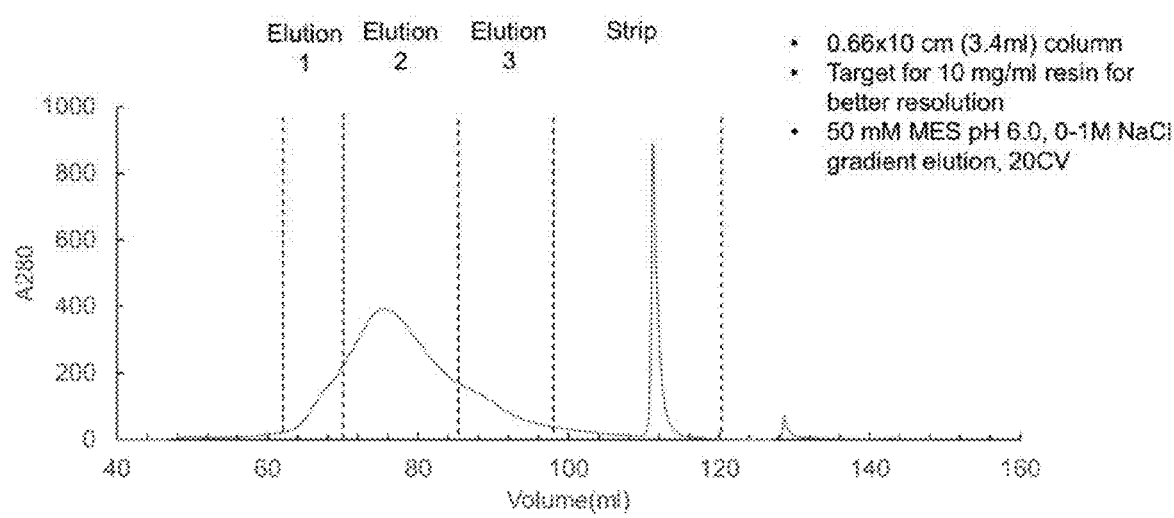
FIG. 17A is a plot of PTH-66 gradient elution using Capto MMC ImpRes.
Figure 17B:
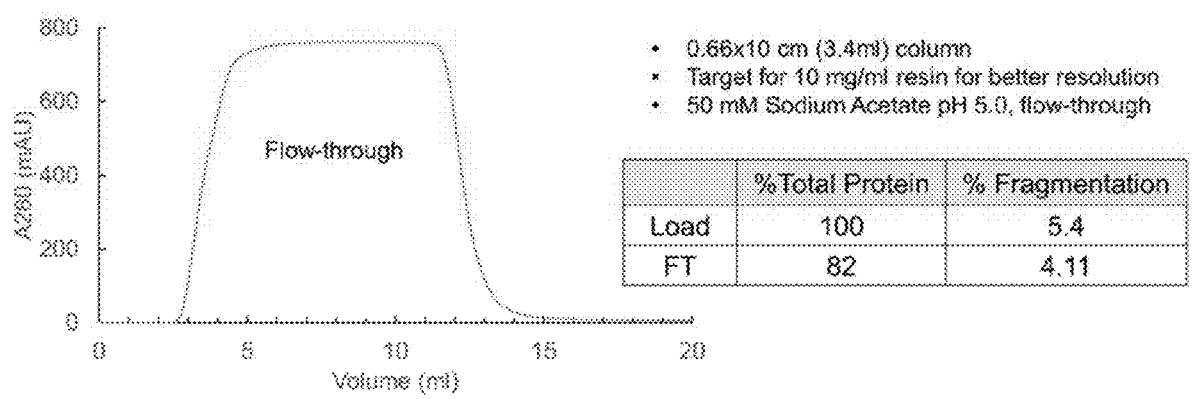
FIG. 17B is a plot of PTH-66 flow-through using Capto Adhere ImpRes.
Figure 18A:
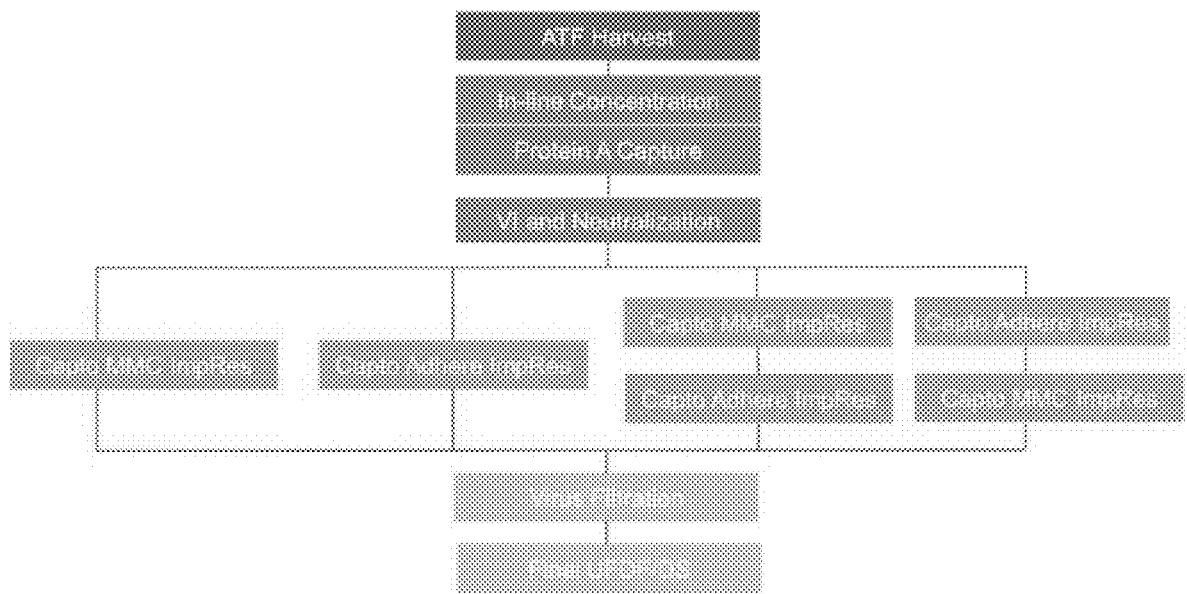
FIG. 18A depicts the downstream polishing step design for PTH-66.
Figure 18B:
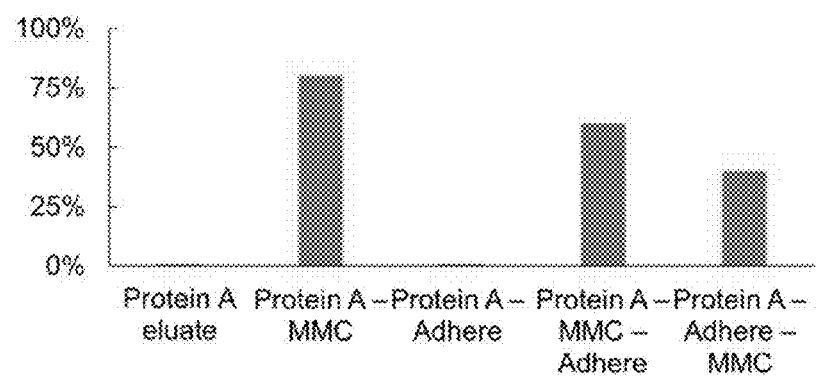
FIG. 18B is a graph showing process robustness with stable pool based on impurity clearance and process yield.
Figure 19A:
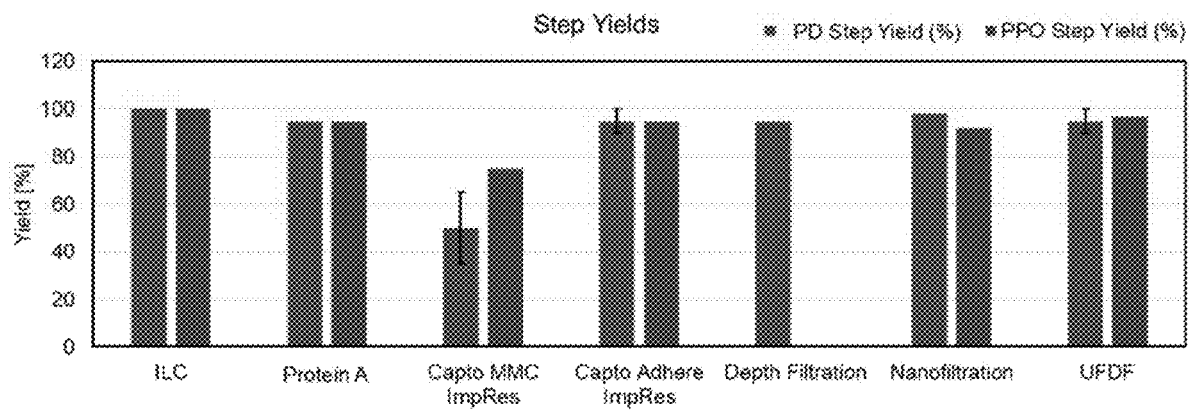
FIGS. 19A-F depict the step yield from the pilot plant operation for the purification of PTH-66 as compared with the yield from process development for the pilot scale production of PTH-66.
Figure 19B:
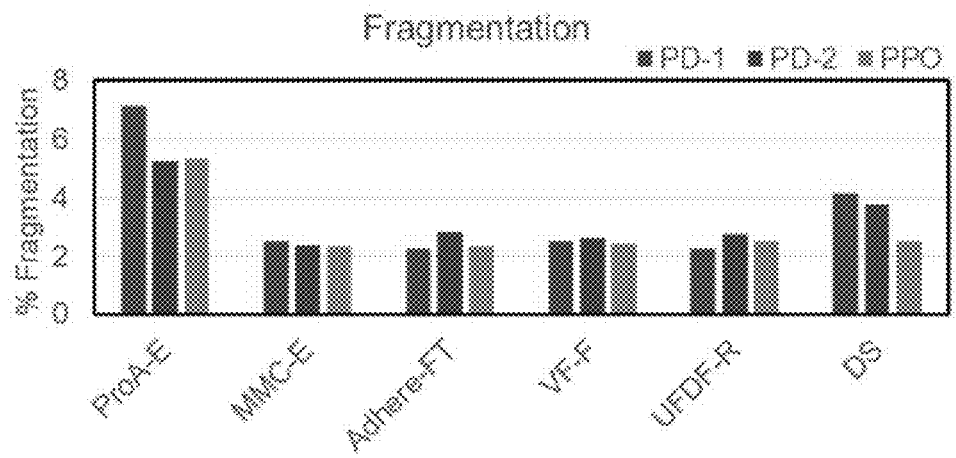
Figure 19C:
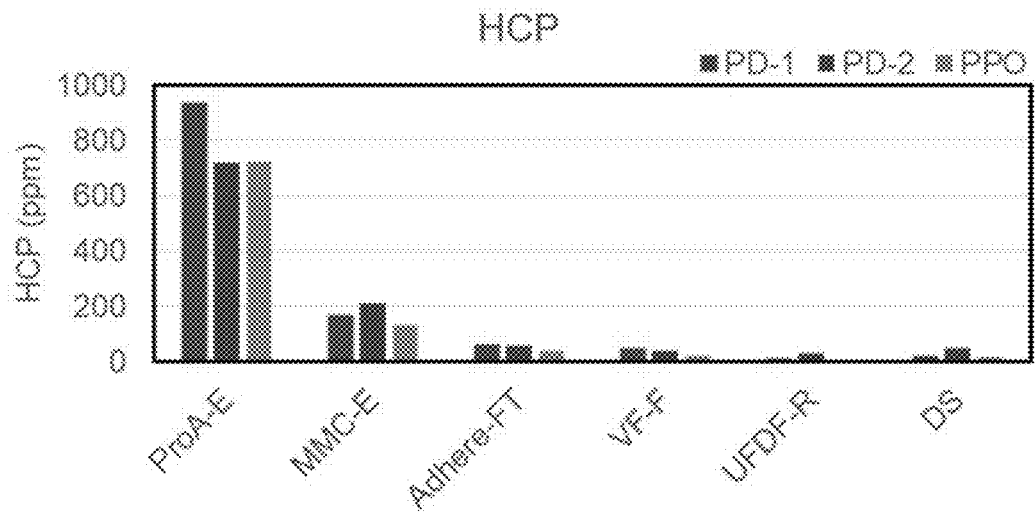
Figure 19D:
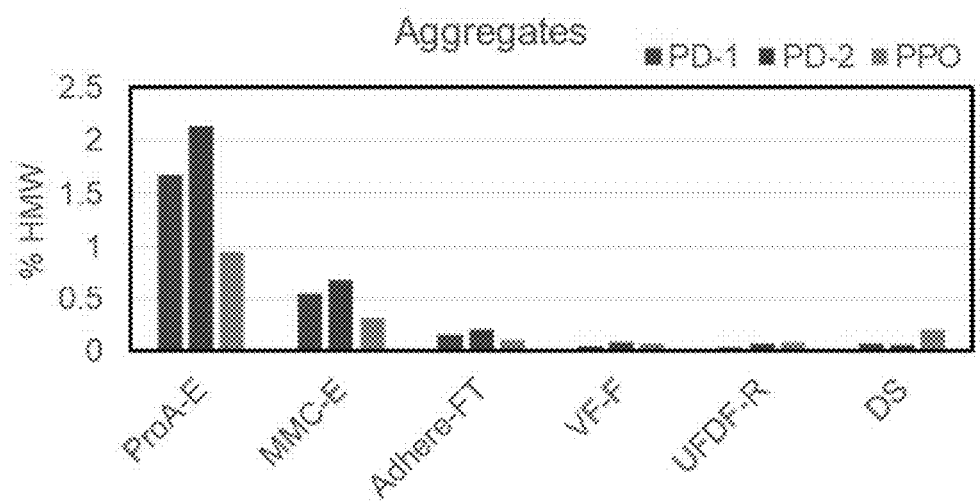
Figure 19E:
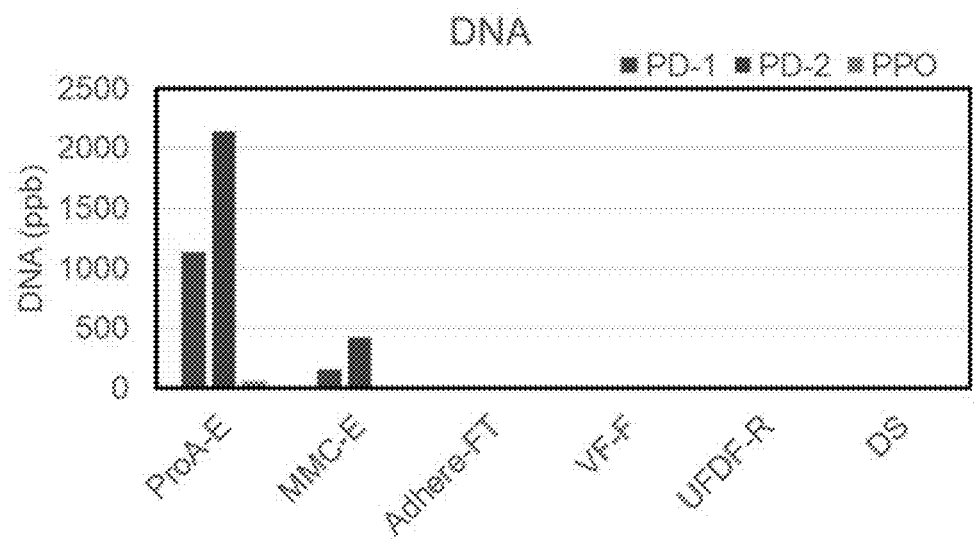
Figure 19F:
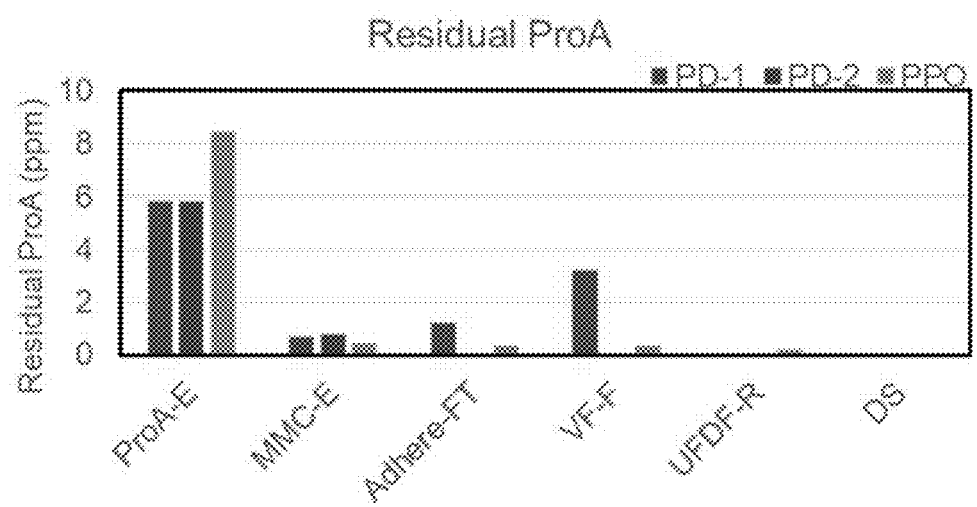

The conditions from high-throughput studies were successfully transferred to bench scale, as shown in FIGS. 17-19. Capto MMC ImpRes gradient elution trace is depicted in FIG. 14A. Better resolution was achieved with 0.66×10 cm (3.4 mL) column, with 50 mM MES at pH 6.0, with 0 to 1M NaCl gradient elution. MMC effectively provides HCP, DNA, BMW, and clipped species removal.

TABLE 3

Capto MMC ImpRes gradient elution

| | Conductivity (mS/cm) | % Total PTH-66 Protein | % Fragmentation |
|---|---|---|---|
| Load | n/a | 100 | 5.48 |
| Elution 1 | 32-42 | 8.2 | 34.79 |
| Elution 2 | 42-62 | 54.1 | 2.35 |
| Elution 3 | 62-76 | 14.8 | 1.06 |

MMC wash steps have been investigated to reduce other process- and product-related impurities. MMC wash optimization is depicted in Table 4. Optimal wash conditions have been determined to be 6 CV of 200 mM NaCl and 3 CV of 250 mM NaCl.

TABLE 4

MMC Wash Optimization

| | | MMC Wash Optimization Run # | | | | | | |
|---|---|---|---|---|---|---|---|---|
| | | 1 | 2 | 3 | 4 | 5 | 6 | 7 |
| Loading | | | | 30 g/L resin | | | 20 g/L resin | |
| Wash 1 | mM | — | — | — | 200 | 200 | 200 | 200 |
| | CV | | | | 3 | 3 | 3 | 6 |
| Wash 2 | mM | — | — | 250 | 250 | 250 | 250 | 250 |
| | CV | | | 3 | 3 | 3 | 3 | 3 |
| Wash 3 | mM | 320 | 300 | — | 300 | — | — | — |
| | CV | 5 | 3 | | 3 | | | |
| Product Quality | | | | | | | | |
| % Yield | | 27 | 44 | 62 | 35 | 54 | 74 | 62 |
| % Decrease in DNA | | 57 | 68 | 73 | 85 | 89 | 82 | |

TABLE 4-continued

MMC Wash Optimization

| | MMC Wash Optimization Run # | | | | | | |
|---|---|---|---|---|---|---|---|
| | 1 | 2 | 3 | 4 | 5 | 6 | 7 |
| % Decrease in HCP | 71 | 71 | 66 | 81 | 77 | 74 | 83 |
| % HMW | <5% | | | | | | |
| Fragmentation | <10% | | | | | | |

Capto Adhere ImpRes flow-through, depicted at FIG. 17B and shown in Table 5, below, shows to provide additional HCP and UMW removal capability. Better resolution was achieved with 0.66×10 cm (3.4 mL) column, with 50 mM sodium acetate buffer at pH 5.0 flow-through.

TABLE 5

Capto Adhere ImpRes Flow-Through

| | % Total PTH-66 Protein | % Fragmentation |
|---|---|---|
| Load | 100 | 5.4 |
| Flow-Through | 82 | 4.11 |

The downstream polishing step design is depicted in FIG. 18A. Process robustness with stable pool based on impurity clearance and process yield is shown in FIG. 15B, as well as in Table 6, below.

TABLE 6

Process Robustness

| Attribute | Test | Release Spec |
|---|---|---|
| Process-Related Impurities | CHO Host Cell DNA | <100 ppb |
| | CHO Host Cell Protein | <200 ppm |
| | Residual ProA | <5 ppm |
| Product-Related Impurities | HMW | <5% |
| | N-term Clipping | <10% |

Pilot-scale production quality attributes are characterized in FIG. 19A-F. As shown in these figures, pilot plant operation (PPO), a large scale purification, has step yields that are comparable to the yields from process development (PD), which is a small lab scale. By comparing these two yields it can be concluded that the purification process has been successfully scaled up using parameters shown above.

The stability of the in-process samples was determined by holding MMC eluate and Adhere FT at ambient temperature and 4-8° C. for 5 and 4 days respectively, followed by analyzing with SEC-HPLC and Intact Mass analysis.

Thus, the Fc-fusion protein fragmentation issue has been successfully addressed using multimodal chromatography and step elution from linear gradient to achieve relatively high recovery without compromising robust impurity clearance has been established.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

What is claimed is:

1. A parathyroid hormone (PTH)-Fc fusion protein, wherein the PTH-Fc fusion protein is PTH-66 having the amino acid sequence of SEQ ID NO: 8.

2. The PTH-Fc fusion protein of claim 1, wherein the PTH-Fc fusion protein is glycosylated.

3. A pharmaceutical composition comprising the PTH-Fc fusion protein of claim 1 and a pharmaceutically acceptable carrier.

4. A pharmaceutical dosage form comprising the PTH-Fc fusion protein of claim 1.

5. The pharmaceutical dosage form of claim 4, wherein the dosage form is a liquid dosage form suitable for administration by injection or infusion.

* * * * *

```
                        SEQUENCE LISTING

<160> NUMBER OF SEQ ID NOS: 13

<210> SEQ ID NO 1
<211> LENGTH: 84
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 2
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
        100                 105                 110

Glu Lys Thr Ile Ser Lys Ala Lys Gly Gln Pro Arg Glu Pro Gln Val
    115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
        180                 185                 190
```

```
Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Glu Thr Pro Ala Gln Leu Leu Phe Leu Leu Leu Leu Trp Leu Pro
1               5                   10                  15

Asp Thr Thr Gly
            20

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Glu Phe Gly Leu Ser Trp Leu Phe Leu Val Ala Ile Leu Lys Gly
1               5                   10                  15

Val Gln Cys

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Pro Leu Leu Leu Leu Leu Pro Leu Leu Trp Ala Gly Ala Leu Ala
1               5                   10                  15

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Asn Leu Tyr Phe Gln Ser His His His His His
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 7

Glu Asn Leu Tyr Phe Gln
1               5

<210> SEQ ID NO 8
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Glu Thr Pro Ala Gln Leu Leu Phe Leu Leu Leu Trp Leu Pro
1               5                   10                  15

Asp Thr Thr Gly Ser Val Ser Glu Ile Gln Leu Met His Asn Leu Gly
                20                  25                  30

Lys His Leu Asn Ser Met Glu Arg Val Glu Trp Leu Arg Lys Lys Leu
            35                  40                  45

Gln Asp Val His Asn Ala Ser Ala Leu Gly Ala Pro Leu Ala Pro Arg
    50                  55                  60

Asp Ala Gly Ser Gln Arg Pro Arg Lys Lys Glu Asp Asn Val Leu Val
65                  70                  75                  80

Glu Ser His Glu Lys Ser Leu Gly Glu Ala Asp Lys Ala Asp Asp Lys
                85                  90                  95

Thr His Thr Cys Pro Pro Cys Pro Ala Pro Glu Ala Ala Gly Gly Pro
            100                 105                 110

Ser Val Phe Leu Phe Pro Pro Lys Pro Lys Asp Thr Leu Met Ile Ser
        115                 120                 125

Arg Thr Pro Glu Val Thr Cys Val Val Val Asp Val Ser His Glu Asp
    130                 135                 140

Pro Glu Val Lys Phe Asn Trp Tyr Val Asp Gly Val Glu Val His Asn
145                 150                 155                 160

Ala Lys Thr Lys Pro Arg Glu Glu Gln Tyr Asn Ser Thr Tyr Arg Val
                165                 170                 175

Val Ser Val Leu Thr Val Leu His Gln Asp Trp Leu Asn Gly Lys Glu
            180                 185                 190

Tyr Lys Cys Lys Val Ser Asn Lys Ala Leu Pro Ala Pro Ile Glu Lys
        195                 200                 205

Thr Ile Ser Lys Ala Lys Gly Gln Pro Arg Glu Pro Gln Val Tyr Thr
    210                 215                 220

Leu Pro Pro Ser Arg Asp Glu Leu Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Lys Leu Thr Val Asp Lys
        275                 280                 285

Ser Arg Trp Gln Gln Gly Asn Val Phe Ser Cys Ser Val Met His Glu
    290                 295                 300

Ala Leu His Asn His Tyr Thr Gln Lys Ser Leu Ser Leu Ser Pro Gly
305                 310                 315                 320

<210> SEQ ID NO 9

<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Glu Thr Pro Ala Gln Leu Leu Phe Leu Leu Leu Leu Trp Leu Pro
1               5                   10                  15

Asp Thr Thr Gly Ser Val Ser Glu Ile Gln Leu Met His Asn Leu Gly
            20                  25                  30

Lys His Leu Asn Ser Met Glu Arg Val Glu Trp Leu Arg Lys Lys Leu
        35                  40                  45

Gln Asp Val His Asn Ala Ser Ala Leu Gly Ala Pro Leu Ala Pro Arg
    50                  55                  60

Asp Ala Gly Ser Gln Arg Pro Arg Lys Lys Glu Asp Asn Val Leu Val
65                  70                  75                  80

Glu Ser His Glu Asp Lys Thr His Thr Cys Pro Pro Cys Pro Ala Pro
                85                  90                  95

Glu Ala Ala Gly Gly Pro Ser Val Phe Leu Phe Pro Pro Lys Pro Lys
            100                 105                 110

Asp Thr Leu Met Ile Ser Arg Thr Pro Glu Val Thr Cys Val Val Val
        115                 120                 125

Asp Val Ser His Glu Asp Pro Glu Val Lys Phe Asn Trp Tyr Val Asp
    130                 135                 140

Gly Val Glu Val His Asn Ala Lys Thr Lys Pro Arg Glu Glu Gln Tyr
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Ala Leu
            180                 185                 190

Pro Ala Pro Ile Glu Lys Thr Ile Ser Lys Ala Lys Gly Gln Pro Arg
        195                 200                 205

Glu Pro Gln Val Tyr Thr Leu Pro Pro Ser Arg Asp Glu Leu Thr Lys
    210                 215                 220

Asn Gln Val Ser Leu Thr Cys Leu Val Lys Gly Phe Tyr Pro Ser Asp
225                 230                 235                 240

Ile Ala Val Glu Trp Glu Ser Asn Gly Gln Pro Glu Asn Asn Tyr Lys
                245                 250                 255

Thr Thr Pro Pro Val Leu Asp Ser Asp Gly Ser Phe Phe Leu Tyr Ser
            260                 265                 270

Lys Leu Thr Val Asp Lys Ser Arg Trp Gln Gln Gly Asn Val Phe Ser
        275                 280                 285

Cys Ser Val Met His Glu Ala Leu His Asn His Tyr Thr Gln Lys Ser
    290                 295                 300

Leu Ser Leu Ser Pro Gly
305                 310

<210> SEQ ID NO 10
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Thr Pro Ala Gln Leu Leu Phe Leu Leu Leu Trp Leu Pro
1               5                   10                  15

Asp Thr Thr Gly Ser Val Ser Glu Ile Gln Leu Met His Asn Leu Gly
            20                  25                  30

Lys His Leu Asn Ser Met Glu Arg Val Glu Trp Leu Arg Lys Lys Leu
        35                  40                  45

Gln Asp Val His Asn Ala Ser Ala Leu Gly Ala Pro Leu Ala Pro Arg
50                  55                  60

Asp Ala Gly Ser Gln Arg Pro Arg Lys Lys Asp Lys Thr His Thr Cys
65                  70                  75                  80

Pro Pro Cys Pro Ala Pro Glu Ala Ala Gly Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Ser His Glu Asp Pro Glu Val Lys
        115                 120                 125

Phe Asn Trp Tyr Val Asp Gly Val Glu Val His Asn Ala Lys Thr Lys
130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Asp Glu Leu Thr Lys Asn Gln Val Ser Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly
290                 295                 300

```
<210> SEQ ID NO 11
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11
```

Met Glu Thr Pro Ala Gln Leu Leu Phe Leu Leu Leu Trp Leu Pro
1               5                   10                  15

Asp Thr Thr Gly Ser Val Ser Glu Ile Gln Leu Met His Asn Leu Gly
            20                  25                  30

Lys His Leu Asn Ser Met Glu Arg Val Glu Trp Leu Arg Lys Lys Leu
        35                  40                  45

Gln Asp Val His Asn Ala Ser Ala Leu Gly Ala Pro Leu Ala Pro Arg

```
              50                  55                  60
Asp Lys Thr His Thr Cys Pro Pro Cys Pro Ala Pro Glu Ala Ala Gly
 65                  70                  75                  80

Gly Pro Ser Val Phe Leu Phe Pro Pro Lys Pro Lys Asp Thr Leu Met
                 85                  90                  95

Ile Ser Arg Thr Pro Glu Val Thr Cys Val Val Val Asp Val Ser His
            100                 105                 110

Glu Asp Pro Glu Val Lys Phe Asn Trp Tyr Val Asp Gly Val Glu Val
            115                 120                 125

His Asn Ala Lys Thr Lys Pro Arg Glu Glu Gln Tyr Asn Ser Thr Tyr
130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Ala Leu Pro Ala Pro Ile
                165                 170                 175

Glu Lys Thr Ile Ser Lys Ala Lys Gly Gln Pro Arg Glu Pro Gln Val
            180                 185                 190

Tyr Thr Leu Pro Pro Ser Arg Asp Glu Leu Thr Lys Asn Gln Val Ser
            195                 200                 205

Leu Thr Cys Leu Val Lys Gly Phe Tyr Pro Ser Asp Ile Ala Val Glu
    210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Lys Leu Thr Val
                245                 250                 255

Asp Lys Ser Arg Trp Gln Gln Gly Asn Val Phe Ser Cys Ser Val Met
            260                 265                 270

His Glu Ala Leu His Asn His Tyr Thr Gln Lys Ser Leu Ser Leu Ser
            275                 280                 285

Pro Gly
    290

<210> SEQ ID NO 12
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Glu Thr Pro Ala Gln Leu Leu Phe Leu Leu Leu Leu Trp Leu Pro
  1               5                  10                  15

Asp Thr Thr Gly Ser Val Ser Glu Ile Gln Leu Met His Asn Leu Gly
                 20                  25                  30

Lys His Leu Asn Ser Met Glu Arg Val Glu Trp Leu Arg Lys Lys Leu
             35                  40                  45

Gln Asp Val His Asn Ala Ser Ala Leu Gly Ala Pro Leu Ala Pro Arg
 50                  55                  60

Asp Ala Gly Ser Gln Arg Pro Arg Lys Lys Glu Asp Asn Val Leu Val
 65                  70                  75                  80

Glu Ser His Glu Lys Ser Leu Gly Glu Ala Asp Lys Ala Asp Val Asn
                 85                  90                  95

Leu Thr Lys Ala Lys Ser Gln Asp Lys Thr His Thr Cys Pro Pro Cys
            100                 105                 110
```

```
Pro Ala Pro Glu Ala Ala Gly Gly Pro Ser Val Phe Leu Phe Pro Pro
            115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5
```